United States Patent
Adsool

(10) Patent No.: US 11,702,425 B2
(45) Date of Patent: Jul. 18, 2023

(54) BICYCLIC COMPOUNDS AS KINASE MODULATORS, METHODS AND USES THEREOF

(71) Applicant: Agency for Science, Technology and Research, Singapore (SG)

(72) Inventor: Vikrant Arun Adsool, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 28 days.

(21) Appl. No.: 17/265,175

(22) PCT Filed: Jul. 23, 2019

(86) PCT No.: PCT/SG2019/050355
§ 371 (c)(1),
(2) Date: Feb. 1, 2021

(87) PCT Pub. No.: WO2020/027723
PCT Pub. Date: Feb. 6, 2020

(65) Prior Publication Data
US 2021/0309668 A1    Oct. 7, 2021

(30) Foreign Application Priority Data
Aug. 1, 2018 (SG) .............. 10201806566V

(51) Int. Cl.
| | | |
|---|---|---|
| *C07D 491/08* | (2006.01) | |
| *C07D 215/233* | (2006.01) | |
| *C07D 401/12* | (2006.01) | |
| *C07D 451/06* | (2006.01) | |
| *C07D 451/14* | (2006.01) | |

(52) U.S. Cl.
CPC ....... *C07D 491/08* (2013.01); *C07D 215/233* (2013.01); *C07D 401/12* (2013.01); *C07D 451/06* (2013.01); *C07D 451/14* (2013.01)

(58) Field of Classification Search
CPC .............. C07D 491/08; C07D 215/233; C07D 401/12; C07D 451/06; C07D 451/14
See application file for complete search history.

(56) References Cited

U.S. PATENT DOCUMENTS

| | | |
|---|---|---|
| 2004/0242603 A1 | 12/2004 | Fujiwara et al. |
| 2012/0123126 A1 | 5/2012 | Chen |

FOREIGN PATENT DOCUMENTS

| | | | | |
|---|---|---|---|---|
| CN | 102086211 A | 6/2011 | | |
| CN | 107778287 A | 3/2018 | | |
| WO | WO-2005030140 A2 * | 4/2005 | ............. | A61K 31/47 |
| WO | WO-2007/146824 A2 | 12/2007 | | |
| WO | WO-2018107072 A1 * | 6/2018 | ........... | A61K 31/437 |
| WO | WO-2020228478 A1 * | 11/2020 | ............. | A61P 35/00 |

OTHER PUBLICATIONS

Cabozantinib, FDA Approved Prescribing Information, Apr. 2016, 21 pages. (Year: 2016).*
Costantino; Bioorganic & Medicinal Chemistry 2001, 9, 221-227. https://doi.org/10.1016/S0968-0896(00)00270-4 (Year: 2001).*
Goh; ACS Med. Chem. Lett. 2017, 8, 516-520. http://dx.doi.org/10.1021/acsmedchemlett.7b00018 (Year: 2017).*
Pellicciari; J. Med. Chem. 1996, 39, 2874-2876. https://doi.org/10.1021/jm960254o (Year: 1996).*
Stepan; J Med Chem. 2012, 55, 3414-3424. https://doi.org/10.1021/jm300094u (Year: 2012).*
Thirumoorthi; Org. Biomol. Chem., 2016, 14, 9485-9489. https://doi.org/10.1039/C6OB01799A (Year: 2016).*
Thirumoorthi; Chem. Commun., 2015,51, 3139-3142. https://doi.org/10.1039/C4CC09655J (Year: 2015).*
Caputo et al., "Synthesis and applications of highly functionalized 1-halo-3-substituted bicyclo[1.1.1]pentanes." Chemical Science, vol. 9, pp. 5295-5300 (May 2018).

* cited by examiner

*Primary Examiner* — Daniel R Carcanague
(74) *Attorney, Agent, or Firm* — Foley & Lardner LLP

(57) ABSTRACT

The present disclosure relates to derivatives of bicyclic compounds and their uses in therapy. In particular, the present disclosure relates to derivatives of bicyclic compounds for use in modulating kinase enzymatic activity and accordingly modulating kinase-dependent diseases and conditions such as cancer and in specific embodiments, hepatocellular carcinoma (HCC). The present disclosure also relates to methods of synthesizing these compounds.

15 Claims, No Drawings

BICYCLIC COMPOUNDS AS KINASE MODULATORS, METHODS AND USES THEREOF

CROSS-REFERENCE TO RELATED APPLICATIONS

The present application is the U.S. National Stage of International Application PCT/SG2019/050355, filed Jul. 23, 2019, and claims priority to Singapore Patent Application No. 10201806566V, filed Aug. 1, 2018.

FIELD

The present disclosure relates to bicyclic compounds and their uses in therapy. In particular, the present disclosure relates to bicyclic compounds for use in modulating kinase enzymatic activity and accordingly modulating kinase-dependent diseases and conditions such as cancer and in specific embodiments, hepatocellular carcinoma (HCC). The present disclosure also relates to methods of synthesizing these compounds.

BACKGROUND

Cancer can be defined as an abnormal growth of cells characterized by a loss of cellular differentiation. Cancer is caused due to abnormalities in the signalling pathways involved in cell proliferation, cell survival, and cell death. According to a World Health Organisation, cancer is a leading cause of death accounting for 8.8 million deaths worldwide in 2015. Among these cancers, liver cancer, or hepatocellular carcinoma (HCC), is the second major cause of cancer deaths. The global HCC toll in 2015 was 788,000 deaths. In Singapore, HCC is the third leading cause of cancer deaths in male patients and fourth in female patients. HCC is projected to be a cancer with second highest mortality rate by 2030.

The current and projected number of HCC patients is a cause for a major concern since the current HCC treatments are very limited. Firstly, the prognosis of HCC is poor, with the world-wide frequency rate almost equalling the mortality rate. Secondly, after diagnosis, the median survival time of stage-C patient is four to eight months. Unfortunately, HCC is relatively more resistant to chemotherapy and outcomes using chemotherapy are not satisfactory. HCC patients often have underlying hepatic dysfunction which makes chemotherapy even less efficacious in these patients.

Currently, tyrosine kinase inhibitor Sorafenib is widely used as a first-line treatment for HCC. The said drug is effective in suppressing angiogenesis and tumour progression. However, the median survival rate with Sorafenib is only about 10.7 months, and studies have shown that the drug increased survival rate only by 2.8 months as compared to a placebo. Moreover, about a quarter of patients have no benefit from Sorafenib due to primary resistance. A decade after Sorafenib's approval, Regorafenib (Stivarga) and Nivolumab (Opdivo) were approved in 2017 as second-line treatments for patients who tolerated Sorafenib, but had progressive disease while on Sorafenib treatment. However, the median overall survival for patients taking Stivarga (Regorafenib) was only about 10.6 months, compared to 7.8 months for patients taking a placebo. In 2019 January, Cabozantinib was approved by USFDA for hepatocellular carcinoma (HCC) in patients previously treated with Sorafenib. In a randomized (2:1), double-blind, placebo-controlled trial with HCC patients who had previously received Sorafenib and had Child Pugh Class A liver impairment, the median progression free survival (PFS) was 5.2 months (4.0, 5.5) and 1.9 months (1.9, 1.9), in the Cabozantinib and placebo arms, respectively (HR 0.44; 95% CI: 0.36, 0.52; p<0.001). The median overall survival (OS) was 10.2 months (95% CI: 9.1, 12.0) for patients receiving Cabozantinib and 8 months (95% CI: 6.8, 9.4) for patients receiving placebo (HR 0.76; 95% CI: 0.63, 0.92; p=0.0049). Objective response rate (ORR) was 4% (95% CI: 2.3, 6.0) in the Cabozantinib arm and 0.4% (95% CI: 0.0, 2.3) in the placebo arm. The most commonly observed adverse reactions in ≥25% of patients who received Cabozantinib in clinical trials, in order of increasing frequency, are vomiting, hypertension, nausea, palmar-plantar erythrodysesthesia, decreased appetite, fatigue, and diarrhoea. Cabozantinib was also linked with a higher incidence of adverse events (AEs) when compared to Regorafenib. Clearly, there is a major unmet need for alternative and improved drug therapies that are suitable to treat hepatocellular carcinoma.

Many of the 538 protein kinases that transfer a γ-phosphate group from ATP to serine, threonine, or tyrosine residues are associated with human cancer initiation and progression. As a consequence, several small-molecule kinase inhibitors have been developed in recent times for the treatment of diverse types of cancer. This approach has been proven to be successful in clinical therapy. Not surprisingly, protein kinases are one of the most targeted group of drug targets and since the 1980s, 37 kinase inhibitors have received FDA approval for treatment of cancers such as breast and lung cancer. Moreover, around 150 kinase-targeted drugs are currently in clinical phase trials. Nevertheless, many factors such as tumour genetics, immunity, drug resistance, tumour microenvironment, and pharmacogenomics determine how useful a compound will be in the treatment of a given cancer. Most if not all of the approved kinase inhibitors have a unique signature of multiple kinase inhibition. Although the subtle differences in the inhibition of multiple kinases are not fully understood it is agreed that the advantage of targeting more than one kinase, increases potency due to the synergistic effect and may also reduce the possibility of developing drug resistance. Interestingly, several multitarget agents were originally designed as single kinase inhibitors and later found to inhibit multiple kinases because of the structural homology among the ATP-binding site of kinases. A multitargeted approach, wherein the ability of a single small molecule protein kinase inhibitor to target multiple kinase pathways has gained increasing attention in recent times. For example, Sorafenib is a multikinase inhibitor targeting Raf serine/threonine kinases as well as different receptor tyrosine kinases including tyrosine-protein kinase Kit (c-Kit), Fms-like tyrosine kinase 3 (FLT-3), Vascular endothelial growth factor receptor (VEGFR) and platelet-derived growth factor receptor (PDGFR).

As mentioned above, each kinase inhibitor has a unique signature of multiple kinase inhibition and the subtle differences in the inhibition of multiple kinases are not fully understood. Several successful kinase inhibitors owe their success to inhibition of a specific cocktail of kinases. However, this broad range of kinase activity may be accompanied by 'undesirable' kinases being targeted. For example, several first and second line HCC treatments such as Sorafenib, Regorafenib and Cabozantinib target c-Kit kinase which is not the most common mutation in HCC patients. However, c-Kit inhibition is known to cause adverse effects such as myelosuppression. This is attributed to the drugs targeting 'undesired' kinases in HCC patients such as c-Kit which is essential for the maintenance and survival of hematopoietic stem cells and mast cells. c-Kit tyrosine kinase is inhibited by Cabozantinib (4.6 nM), Sorafenib (68 nM) and Regorafenib (7 nm). Undoubtedly, the issues arising due to the close structural homology of kinases is of significance. Accordingly, there is a need for alternative drug compounds that do not target the undesirable kinases.

SUMMARY OF THE INVENTION

The present invention relates to bicyclic compounds and their use in therapy. In particular, the bicyclic compounds disclosed herein are selective to some kinases and can modulate cellular activities such as differentiation, chemoinvasion, programmed cell death, proliferation, migration and other biological activities associated with invasive and uncontrolled cell growth. Specifically, the bicyclic compounds are able to modulate and/or inhibit the TRK, VEGFR and TAM families of receptor tyrosine kinases. Accordingly, these compounds may be useful in the treatment or inhibition of cancer, and in particular, hepatocellular carcinoma.

In a first aspect, the present invention discloses a compound of formula (I) or a salt, solvate or prodrug thereof:

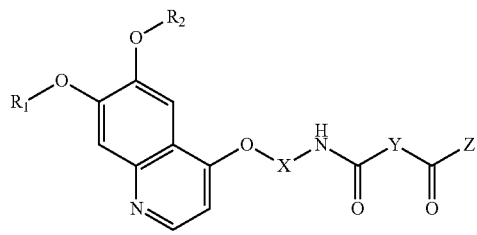

(I)

wherein $R_1$ and $R_2$ are independently selected from optionally substituted alkyl, optionally substituted alkenyl or optionally substituted alkynyl;
X is selected from optionally substituted cycloalkylene, optionally substituted heterocyclylene, optionally substituted arylene or optionally substituted heteroarylene;
Y is optionally substituted cycloalkylene; and
Z is selected from optionally substituted —N-heterocyclyl, optionally substituted —NH(cycloalkyl), optionally substituted —NH(aryl) or optionally substituted —NH(heteroaryl);
wherein when Z is optionally substituted —NH(aryl), then at least one of X and Y is optionally substituted bridged cycloalkylene.

In an embodiment, the present invention discloses a compound of formula (I) or a salt, solvate or prodrug thereof,
wherein $R_1$ and $R_2$ are independently selected from optionally substituted alkyl, optionally substituted alkenyl or optionally substituted alkynyl;
X is selected from optionally substituted cycloalkylene or optionally substituted arylene;
Y is optionally substituted cycloalkylene; and
Z is selected from optionally substituted —N-heterocyclyl or optionally substituted —NH(cycloalkyl).

In an embodiment, $R_1$ and $R_2$ are independently optionally substituted $C_1$-$C_5$ alkyl.

In another embodiment, X is optionally substituted bridged cycloalkylene or optionally substituted arylene. In another embodiment, wherein X is optionally substituted bridged bicycloalkylene or optionally substituted arylene. In another embodiment, X is optionally substituted cycloalkylene or optionally substituted arylene, the cycloalkylene or arylene is selected from:

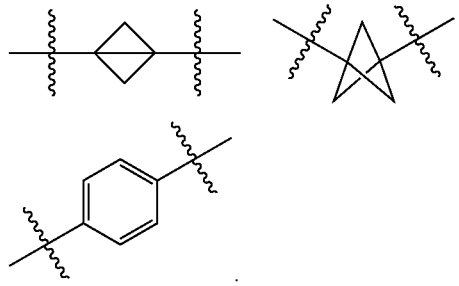

In another embodiment, Y is optionally substituted cycloalkylene, the cycloalkylene is selected from:

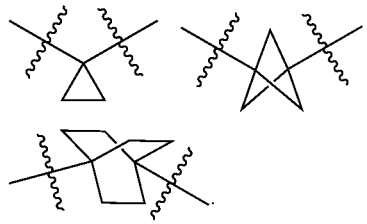

In another embodiment, Z is optionally substituted bridged —N-heterocyclyl or optionally substituted —NH (bridged cycloalkyl). In another embodiment, Z is optionally substituted bridged bicyclic —N-heterocyclyl or optionally substituted —NH(bridged bicycloalkyl). In another embodiment, Z is optionally substituted —N-heterocyclyl or optionally substituted —NH(cycloalkyl), the —N-heterocyclyl or —NH(cycloalkyl) is selected from the following:

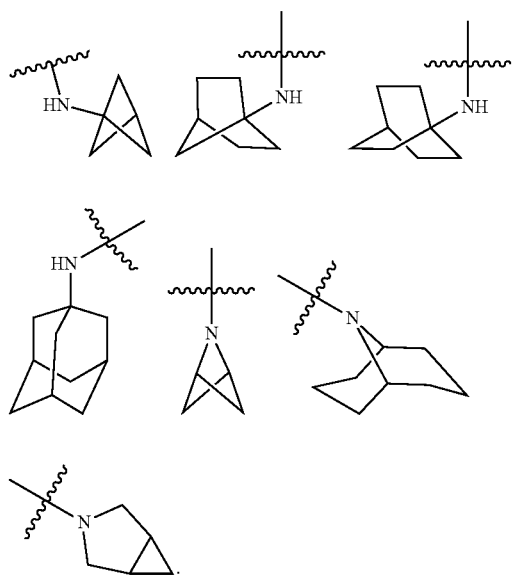

The present invention also discloses a compound of formula (I) or a salt, solvate or prodrug thereof:

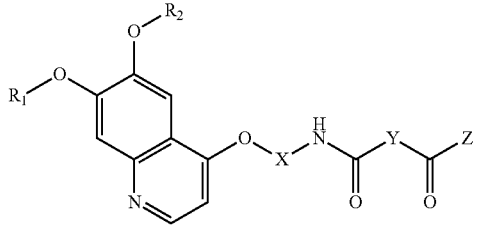
(I)

wherein $R_1$ and $R_2$ are independently selected from optionally substituted alkyl, optionally substituted alkenyl or optionally substituted alkynyl;
X is selected from optionally substituted cycloalkylene, optionally substituted heterocyclylene, optionally substituted arylene or optionally substituted heteroarylene;
Y is optionally substituted cycloalkylene; and
Z is selected from optionally substituted —N-heterocyclyl, optionally substituted —NH(cycloalkyl), optionally substituted —NH(aryl) or optionally substituted —NH(heteroaryl);
wherein at least one of X, Y or Z is an optionally substituted bridged moiety.

In some embodiments, Z is an optionally substituted —NH(bridged cycloalkyl).

In a second aspect, the present invention discloses a pharmaceutical composition comprising an effective amount of a compound of formula (I) or a pharmaceutically acceptable salt, solvate or prodrug thereof:

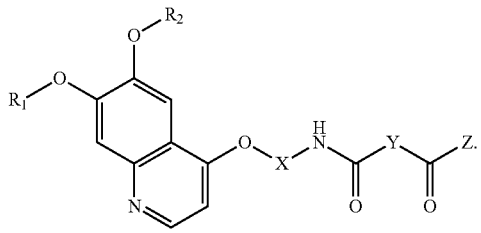
(I)

In a third aspect, the present invention discloses a method for treating cancer in a patient in need thereof, the method comprising administering to the patient a therapeutically effective amount of a compound of formula (I) or a pharmaceutically acceptable salt, solvate or prodrug thereof:

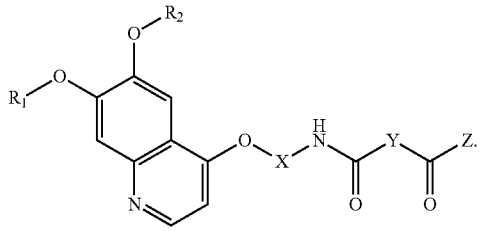
(I)

In a fourth aspect, the present invention discloses a use of a compound of formula (I) or a pharmaceutically acceptable salt, solvate or prodrug thereof:

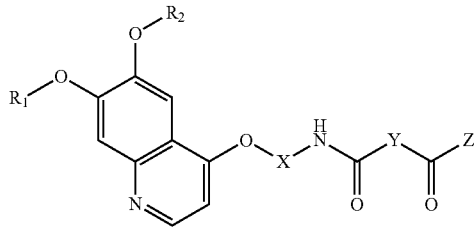
(I)

in the manufacture of a medicament for treating cancer in a patient in need thereof.

In a fifth aspect, the present invention discloses a compound of formula (I) or a pharmaceutically acceptable salt, solvate or prodrug thereof:

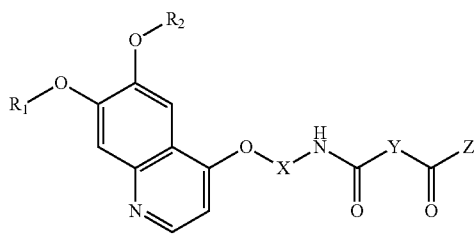
(I)

for use in treating cancer in a patient in need thereof.

In some embodiments, the cancer is hepatocellular carcinoma.

DETAILED DESCRIPTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

"Alkyl" refers to monovalent alkyl groups which may be straight chained or branched and preferably have from 1 to 10 carbon atoms or more preferably 1 to 6 carbon atoms. Examples of such alkyl groups include methyl, ethyl, n-propyl, iso-propyl, n-butyl, iso-butyl, n-hexyl, and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH=CH$_2$), n-propenyl (—CH$_2$CH=CH$_2$), iso-propenyl (—C(CH$_3$)=CH$_2$), but-2-enyl (—CH$_2$CH=CHCH$_3$), and the like.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (—CH$_2$C≡CH), pent-2-ynyl (—CH$_2$C≡CCH$_2$—CH$_3$), and the like.

"Aryl" refers to an unsaturated aromatic carbocyclic group having a single ring (eg. phenyl) or multiple condensed rings (eg. naphthyl or anthryl), preferably having from 6 to 14 carbon atoms. Examples of aryl groups include phenyl, naphthyl and the like.

"Arylene" refers to a divalent aryl group wherein the aryl group is as described above.

"Cycloalkyl" refers to cyclic alkyl groups having a single cyclic ring or multiple condensed rings, preferably incorporating 3 to 16 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, indanyl, 1,2,3,4-tetrahydronapthalenyl and the like. As used herein, 'cycloalkyl' comprises bridged cycloalkyl. Included within the scope of bridged cycloalkyl are fused cycloalkyl. These bridged cycloalkyl may be bicyclic. The skilled person would understand that bridged cycloalkyl comprises two or more rings bonded to each other at bridgehead atoms (ring junctions). In fused bicyclic compounds, two rings share two adjacent atoms; i.e. the rings share one covalent bond or the so-called bridgehead atoms are directly connected. The nomenclature of naming fused bicyclic compounds is with the prefix bicyclo[x.y.0], wherein '0' denotes that the two rings are linked by a covalent bond. In other bridged bicyclic compounds, the two rings can share three or more atoms, i.e. separating the two bridgehead atoms by a bridge containing at least one atom. In this case, the nomenclature of naming bridged bicyclic compounds is with the prefix bicyclo[x.y.z], wherein 'z' denotes that the two rings are linked by z number of atoms between the bridgehead atoms. For example, norbornane, also known as bicyclo[2.2.1]heptane, can be thought of as a pair of cyclopentane rings each sharing three of their five carbon atoms. Examples of bridged cycloalkyl are bicyclo[1.1.1]pentane, bicyclo[2.2.1]heptane, bicyclo[2.2.2]octane, bicyclo[3.3.1]nonane, bicyclo[2.1.1]hexane, bicyclo[4.2.2]decane, bicyclo[1.1.0]butane, α-thujene and bicyclo[4.4.0]decane (decalin).

"Cycloalkylene" refers to a divalent cycloalkyl group wherein the cycloalkyl group is as described above.

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. Accordingly, N-heterocyclyl refers to a heterocyclyl wherein a heteroatom is nitrogen. It will be understood that the N-heterocyclyl group is connected to the core molecule of the compounds of the present invention, through a C-heteroatom bond, in particular a C—N bond (denoted by —N-heterocyclyl). As used herein, N-heterocyclyl includes the bridged cycloalkyl as defined above. Examples of bridged N-heterocyclyl includes amantadine, memantine, hexamine, morphan and DABCO.

"Heterocyclylene" refers to a divalent heterocyclyl group wherein the heterocyclyl group is as described above.

"Heteroaryl" refers to a monovalent aromatic heterocyclic group which fulfils the Hückel criteria for aromaticity (i.e. contains 4n+2 π electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (e.g. pyridyl, pyrrolyl or N-oxides thereof or furyl) or multiple condensed rings (e.g. indolizinyl, benzoimidazolyl, coumarinyl, quinolinyl, isoquinolinyl or benzothienyl). It will be understood that where, for instance, R$_2$ or R' is an optionally substituted heteroaryl which has one or more ring heteroatoms, the heteroaryl group can be connected to the core molecule of the compounds of the present invention, through a C—C or C-heteroatom bond, in particular a C—N bond.

"Heteroarylene" refers to a divalent heteroaryl group wherein the heteroaryl group is as described above.

In this specification "optionally substituted" is taken to mean that a group may or may not be further substituted or fused (so as to form a condensed polycyclic group) with one or more groups selected from hydroxyl, acyl, alkyl, alkoxy, alkenyl, alkenyloxy, alkynyl, alkynyloxy, amino, aminoacyl, thio, arylalkyl, arylalkoxy, aryl, aryloxy, carboxyl, acylamino, cyano, halogen, nitro, phosphono, sulfo, phosphorylamino, phosphinyl, heteroaryl, heteroarylalkyl, heteroaryloxy, heterocyclyl, heterocyclylalkyl, heterocyclyloxy, oxyacyl, oxime, oxime ether, hydrazone, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like, and may also include a bond to a solid support material, (for example, substituted onto a polymer resin). For instance, an "optionally substituted amino" group may include amino acid and peptide residues.

From his own experience and from the literature, the inventor was deeply aware of the issues pertaining to the progress of bioactive compounds due to bioavailability and solubility concerns. To address these issues, he had hypothesized use of sp$^3$ rich building-blocks, such as sp$^3$ rich bicyclo[1.1.1]pentane derivatives, for the synthesis and modification of bioactive molecules. To achieve this end, the inventor had separately developed better synthetic routes to several such building-blocks that were synthetically difficult to achieve or procure, which are incorporated herein by preference (Org. Lett., 2014, 16, 1884; Chem. Comm. 2015, 51, 3139; Org. and Biomol. Chem. 2015, 13, 11597).

It is believed that by tactically modifying bioactive compounds with such sp$^3$ rich building blocks, advantages such as improved water solubility, permeability, bioavailability and metabolism may be achieved. For example, employment of one such sp$^3$ rich building block as a replacement of a phenolic functional group in a bioactive molecule provided an equipotent compound with improved absorption and metabolism properties.

The inventor is also aware of specific issues with selectivity of multi-kinase inhibitors. Specifically, because of the close homology of the constituents of the kinome, there are difficulties in development of multi-kinase inhibitors that do not significantly affect undesirable kinases. The inventor found out that compounds with such sp$^3$ rich building blocks are advantageous to developing multi-kinase inhibitors with specific and desired portfolio of kinase inhibition.

As mentioned above, the present invention relates to bicyclic compounds of formula (I). These compounds were found to have distinctive multikinase activity which are advantageous for treating kinase related diseases and conditions. In particular, the compounds may modulate and/or inhibit the TRK, VEGFR and TAM families of receptor tyrosine kinases. Even more advantageously, the compounds may modulate and/or inhibit the TRK, VEGFR and TAM families of receptor tyrosine kinases while not potently inhibiting c-Kit kinase thus reducing or eliminating the known adverse effects associated with c-Kit inhibition. Accordingly, the compounds are suitable for use in treating diseases or conditions associated with kinase receptor signal transduction pathways, such as but not limited to, diseases or conditions in which cellular activities is characterized (at least in part) by invasion, migration, proliferation and other biological activities associated with invasive and uncontrolled cell growth. For example, these compounds may be useful against specific cancers, such as HCC, based upon their unique multikinase inhibition profile. In this regard, the compounds may have at least similar (if not better) bioavailability compared to current drugs on market and may have reduced or less adverse effects. This advantage is particularly pronounced when the compounds have at least one bridged moiety, for example see Compounds in Table 1.

In an embodiment, the present invention provides a compound of formula (I) or a salt, solvate or prodrug thereof:

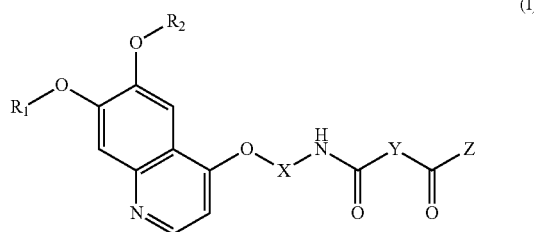

(I)

wherein $R_1$ and $R_2$ are independently selected from optionally substituted alkyl, optionally substituted alkenyl or optionally substituted alkynyl;
X is selected from optionally substituted cycloalkylene, optionally substituted heterocyclylene, optionally substituted arylene or optionally substituted heteroarylene;
Y is optionally substituted cycloalkylene; and
Z is selected from optionally substituted —N-heterocyclyl, optionally substituted —NH(cycloalkyl), optionally substituted —NH(aryl) or optionally substituted —NH(heteroaryl);
wherein when Z is optionally substituted —NH(aryl) or optionally substituted —NH(heteroaryl), then one of X or Y is optionally substituted bridged cycloalkylene.

In an embodiment, the present invention provides a compound of formula (I) or a salt, solvate or prodrug thereof, wherein $R_1$ and $R_2$ are independently selected from optionally substituted alkyl, optionally substituted alkenyl or optionally substituted alkynyl;
X is selected from optionally substituted cycloalkylene or optionally substituted arylene;
Y is optionally substituted cycloalkylene; and
Z is selected from optionally substituted —N-heterocyclyl or optionally substituted —NH(cycloalkyl).

In an embodiment, $R_1$ and $R_2$ are independently $C_1$-$C_5$ alkyl. In another embodiment, the $C_1$-$C_5$ alkyl is methyl. In another embodiment, the $C_1$-$C_5$ alkyl is ethyl. In another embodiment, the $C_1$-$C_5$ alkyl is n-propyl. In another embodiment the $C_1$-$C_5$ alkyl is iso-propyl. In another embodiment, the $C_1$-$C_5$ alkyl is n-butyl. In another embodiment, the $C_1$-$C_5$ alkyl is sec-butyl. In another embodiment, the $C_1$-$C_5$ alkyl is isobutyl. In another embodiment, the $C_1$-$C_5$ alkyl is tert-butyl. In another embodiment, the $C_1$-$C_5$ alkyl is n-pentyl. In another embodiment, the $C_1$-$C_5$ alkyl is 2-methylbutan-2-yl. In another embodiment, the $C_1$-$C_5$ alkyl is 2,2-dimethylpropyl. In another embodiment, the $C_1$-$C_5$ alkyl is 3-methylbutyl. In another embodiment, the $C_1$-$C_5$ alkyl is sec-pentyl. In another embodiment, the $C_1$-$C_5$ alkyl is 3-pentyl. In another embodiment, the $C_1$-$C_5$ alkyl is sec-isopentyl. In another embodiment, the $C_1$-$C_5$ alkyl is 2-methylbutyl.

In an embodiment, Z is selected from optionally substituted —N-heterocyclyl or optionally substituted —NH(cycloalkyl) and optionally substituted with aryl, halo or alkyl. In another embodiment, the optional substitution is phenyl. In another embodiment, the optional substitution is fluoro, chloro, bromo or iodo. In another embodiment, the optional substitution is fluoro. In another embodiment, the optional substitution is $C_1$-$C_5$ alkyl. In another embodiment, the optional substitution is oxymethyl.

In an embodiment, when X is optionally substituted cycloalkylene, Z is selected from optionally substituted —N-heterocyclyl, optionally substituted —NH(cycloalkyl), optionally substituted —NH(aryl) or optionally substituted —NH(heteroaryl). In another embodiment, when X is optionally substituted cycloalkylene, Z is selected from optionally substituted —N-heterocyclyl or optionally substituted —NH(cycloalkyl). In another embodiment, when X is optionally substituted arylene, Z is selected from optionally substituted —N-heterocyclyl, optionally substituted —NH(cycloalkyl) or optionally substituted —NH(heteroaryl). In another embodiment, when X is optionally substituted arylene, Z is selected from optionally substituted —N-heterocyclyl or optionally substituted —NH(cycloalkyl).

In an embodiment, Z is $NR_3R_4$.

Accordingly, in an embodiment, the present invention provides a compound of formula (Ia) or a salt, solvate or prodrug thereof:

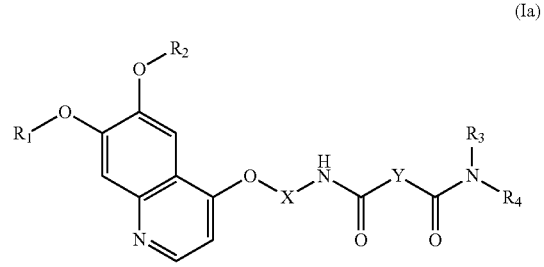

(Ia)

wherein $R_1$ and $R_2$ are independently selected from optionally substituted alkyl, optionally substituted alkenyl or optionally substituted alkynyl;
X is selected from optionally substituted cycloalkylene, optionally substituted heterocyclylene, optionally substituted arylene or optionally substituted heteroarylene;
Y is optionally substituted cycloalkylene; and
when $R_3$ is H, $R_4$ is selected from optionally substituted cycloalkyl, optionally substituted aryl or optionally substituted heteroaryl, or $R_3$ and $R_4$ is linked to form an optionally substituted N-heterocyclyl;
wherein when $R_4$ is optionally substituted aryl, then at least one of X and Y is optionally substituted bridged cycloalkylene.

The present invention provides a compound of formula (Ia) or a salt, solvate or prodrug thereof,
wherein $R_1$ and $R_2$ are independently selected from optionally substituted alkyl, optionally substituted alkenyl or optionally substituted alkynyl;

X is selected from optionally substituted cycloalkylene, optionally substituted heterocyclylene, optionally substituted arylene or optionally substituted heteroarylene;
Y is optionally substituted cycloalkylene; and
when $R_3$ is H, $R_4$ is selected from optionally substituted cycloalkyl, optionally substituted aryl or optionally substituted heteroaryl, or $R_3$ and $R_4$ is linked to form an optionally substituted N-heterocyclyl;
wherein when $R_4$ is optionally substituted aryl or optionally substituted heteroaryl, then one of X or Y is optionally substituted bridged cycloalkylene.

In an embodiment, when X is optionally substituted cycloalkylene, $R_4$ is selected from optionally substituted cycloalkyl, optionally substituted aryl or optionally substituted heteroaryl, or $R_3$ and $R_4$ is linked to form a optionally substituted N-heterocyclyl. In another embodiment, when X is optionally substituted cycloalkylene, $R_4$ is selected from optionally substituted cycloalkyl, or $R_3$ and $R_4$ is linked to form a optionally substituted N-heterocyclyl. In another embodiment, when X is optionally substituted arylene, $R_4$ is selected from optionally substituted cycloalkyl or optionally substituted heteroaryl, or $R_3$ and $R_4$ is linked to form a optionally substituted N-heterocyclyl. In another embodiment, when X is optionally substituted arylene, $R_4$ is selected from optionally substituted cycloalkyl, or $R_3$ and $R_4$ is linked to form an optionally substituted N-heterocyclyl.

In all embodiments, compound of formula (I) or (Ia) is a bridged compound. In this regard, at least one of X, Y, Z, $R_3$ or $R_4$ (if present) is a bridged moiety. For example, the bridged moiety can be a bridged cycloalkyl or cycloalkylene, a bridged heterocyclyl or heterocyclylene. In some embodiments, when the bridged moiety is at Z, Z can be —NH(bridged cycloalkyl) or —NH(bridged heterocyclyl). In some embodiments, when the bridged moiety is at $R_3$ or $R_4$, $R_3$ or $R_4$ can be a bridged cycloalkyl. In some embodiments, $R_3$ and $R_4$ are linked to form a bridged heterocyclyl.

Accordingly in some embodiment, the present invention provides a compound of formula (I) or a salt, solvate or prodrug thereof:

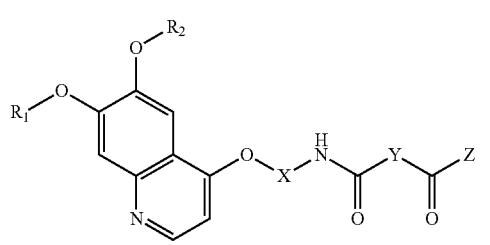

(I)

wherein $R_1$ and $R_2$ are independently selected from optionally substituted alkyl, optionally substituted alkenyl or optionally substituted alkynyl;

X is selected from optionally substituted cycloalkylene, optionally substituted heterocyclylene, optionally substituted arylene or optionally substituted heteroarylene;
Y is optionally substituted cycloalkylene; and
Z is selected from optionally substituted —N-heterocyclyl, optionally substituted —NH(cycloalkyl), optionally substituted —NH(aryl) or optionally substituted —NH(heteroaryl);
wherein at least one of X, Y or Z is an optionally substituted bridged moiety.

In an embodiment, the present invention provides a compound of formula (I) or a salt, solvate or prodrug thereof:

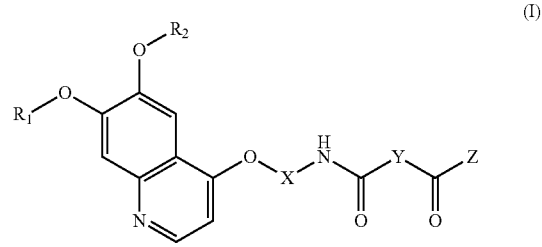

(I)

wherein $R_1$ and $R_2$ are independently selected from optionally substituted alkyl, optionally substituted alkenyl or optionally substituted alkynyl;
X is selected from optionally substituted cycloalkylene, optionally substituted heterocyclylene, optionally substituted arylene or optionally substituted heteroarylene;
Y is optionally substituted cycloalkylene; and
Z is selected from optionally substituted —N-heterocyclyl, optionally substituted —NH(cycloalkyl), optionally substituted —NH(aryl) or optionally substituted —NH(heteroaryl);
wherein at least two of X, Y or Z are optionally substituted bridged moieties.

For example, X and Y can be optionally substituted bridged moieties, or X and Z can be optionally substituted bridged moieties, or Y and Z can be optionally substituted bridged moieties.

In some embodiment, the present invention provides a compound of formula (Ia) or a salt, solvate or prodrug thereof:

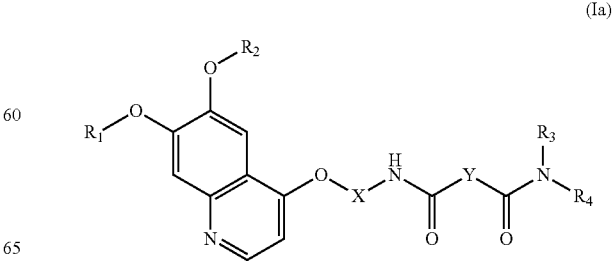

(Ia)

wherein R₁ and R₂ are independently selected from optionally substituted alkyl, optionally substituted alkenyl or optionally substituted alkynyl;

X is selected from optionally substituted cycloalkylene, optionally substituted heterocyclylene, optionally substituted arylene or optionally substituted heteroarylene;

Y is optionally substituted cycloalkylene; and

R₃ is H;

R₄ is selected from optionally substituted cycloalkyl, optionally substituted aryl or optionally substituted heteroaryl;

wherein at least one of X, Y or R⁴ is an optionally substituted bridged moiety.

In an embodiment, the present invention provides a compound of formula (Ia) or a salt, solvate or prodrug thereof:

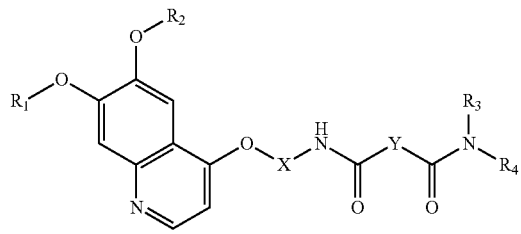

(Ia)

wherein R₁ and R₂ are independently selected from optionally substituted alkyl, optionally substituted alkenyl or optionally substituted alkynyl;

X is selected from optionally substituted cycloalkylene, optionally substituted heterocyclylene, optionally substituted arylene or optionally substituted heteroarylene;

Y is optionally substituted cycloalkylene; and

R₃ is H;

R₄ is selected from optionally substituted cycloalkyl, optionally substituted aryl or optionally substituted heteroaryl;

wherein at least two of X, Y or R⁴ are optionally substituted bridged moieties.

In some embodiments, the optionally substituted bridged moiety is an optionally substituted bridged cycloalkyl or cycloalkylene, selected from the group consisting of bicyclo[1.1.1]pentanyl(ene), bicyclo[2.2.1]heptanyl(ene), bicyclo[2.2.2]octanyl(ene), bicyclo[3.3.1]nonanyl(ene), bicyclo[2.1.1]hexanyl(ene), bicyclo[4.2.2]decanyl(ene), bicyclo[1.1.0]butanyl(ene) and bicyclo[4.4.0]decanyl(ene).

In some embodiments, the present invention provides a compound of formula (Ia) or a salt, solvate or prodrug thereof:

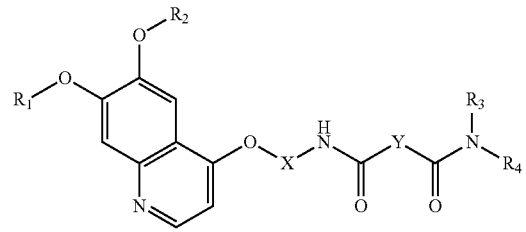

(Ia)

wherein R₁ and R₂ are independently selected from optionally substituted alkyl, optionally substituted alkenyl or optionally substituted alkynyl;

X is selected from optionally substituted cycloalkylene, optionally substituted heterocyclylene, optionally substituted arylene or optionally substituted heteroarylene;

Y is optionally substituted cycloalkylene; and

R₃ is H; and

R₄ is optionally substituted bridged cycloalkyl.

In some embodiments, R₄ is optionally substituted bridged cycloalkyl, selected from the group consisting of bicyclo[1.1.1]pentanyl, bicyclo[2.2.1]heptanyl, bicyclo[2.2.2]octanyl, bicyclo[3.3.1]nonanyl, bicyclo[2.1.1]hexanyl, bicyclo[4.2.2]decanyl, bicyclo[1.1.0]butanyl and bicyclo[4.4.0]decanyl.

In some embodiments,

R₁ and R₂ are independently selected from optionally substituted alkyl, optionally substituted alkenyl or optionally substituted alkynyl;

X is selected from optionally substituted cycloalkylene, optionally substituted heterocyclylene, optionally substituted arylene or optionally substituted heteroarylene;

Y is optionally substituted cycloalkylene; and

R₃ is H; and

R₄ is optionally substituted bicyclo[1.1.1]pentane.

In some embodiments,

R₁ and R₂ are independently selected from optionally substituted alkyl, optionally substituted alkenyl or optionally substituted alkynyl;

X is selected from optionally substituted arylene or optionally substituted heteroarylene;

Y is optionally substituted cycloalkylene; and

R₃ is H; and

R₄ is optionally substituted bicyclo[1.1.1]pentane.

In some embodiments, X, Y and Z (or R₃ and R₄) may be optionally substituted. In some embodiments, Z (or R₃ and R₄) may be optionally substituted. The optional substituent may be selected from the group consisting of halogen, oxy, cyano, alkyl, haloalkyl, aryl, heteroaryl, alkoxy, oxyalkyl, amino, aminoacyl, alkylaminoacyl, dialkylaminoacyl, cycloalkylaminoacyl, acylamino, alkylacylamino, aryloxy, benzyloxy, alkylacyl, oxyacyl and alkoxyacyl.

In an embodiment, compounds of the present invention may be in a dimeric form, as represented by formula (II):

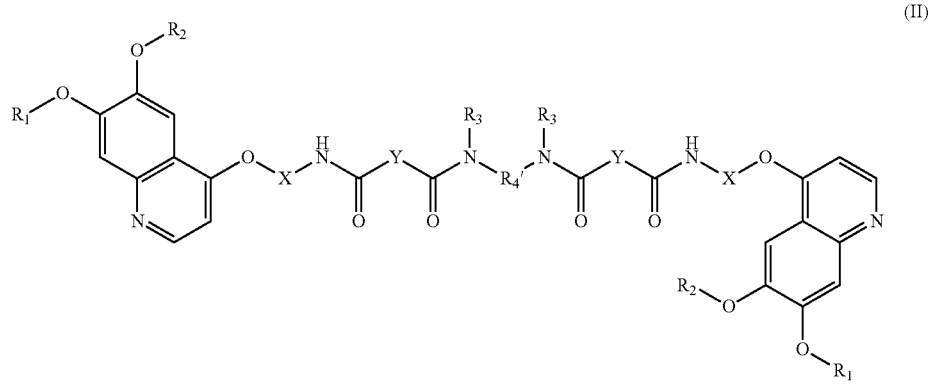

wherein $R_1$, $R_2$, X, Y and $R_3$ are as defined herein; and $R_4'$ is selected from optionally substituted cycloalkylene, optionally substituted arylene or optionally substituted heteroarylene; and wherein at least one of X, Y or $R^4$ is a optionally substituted bridged cycloalkylene.

In some embodiments, the compound of formula (I), (Ia) or (II) may be selected from the following:

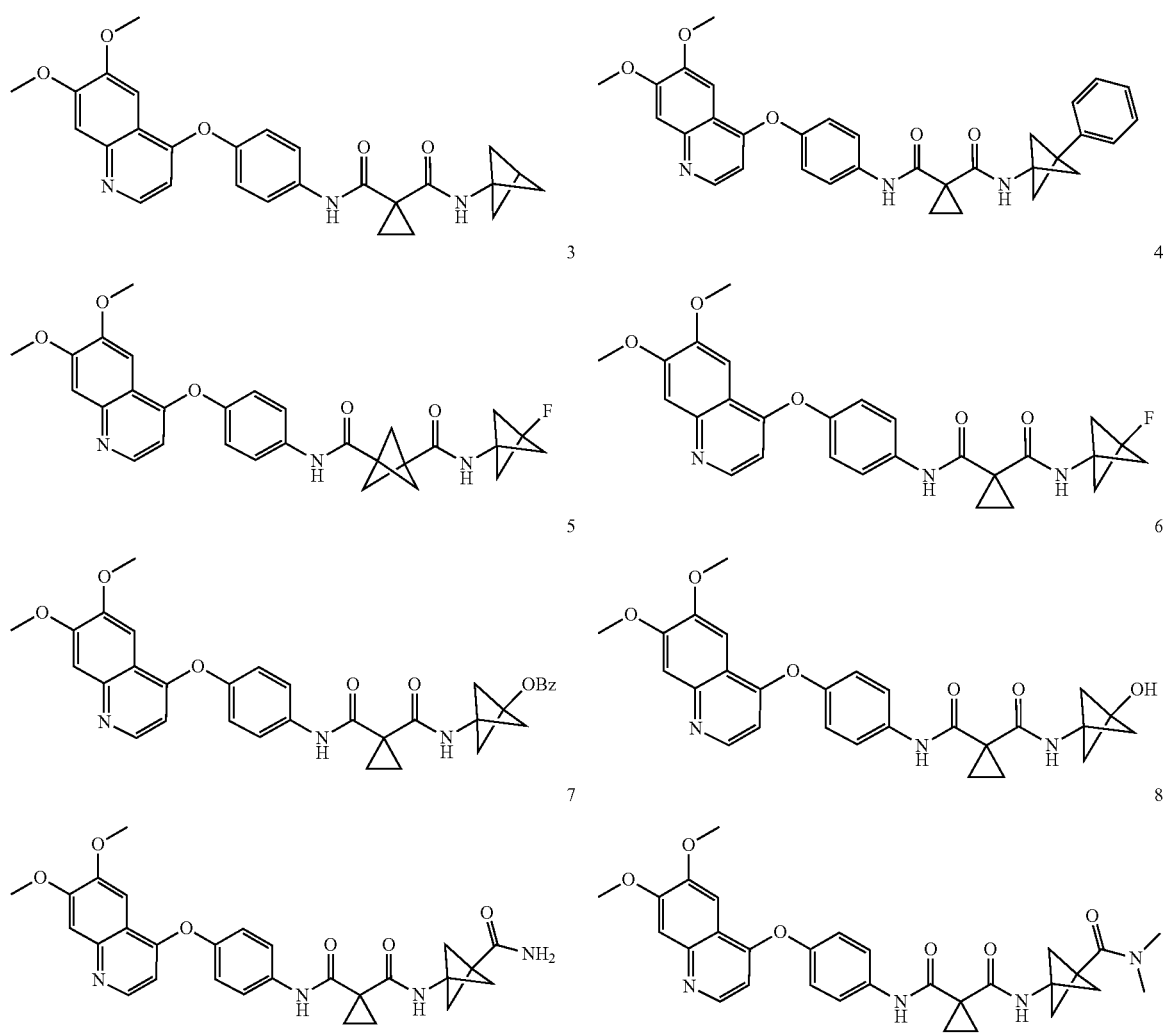

-continued
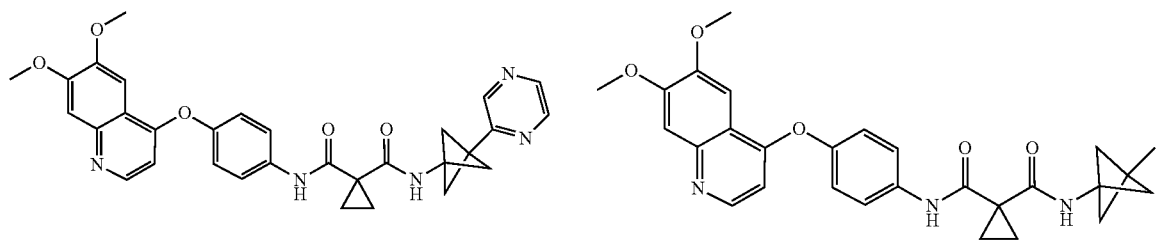
9
10
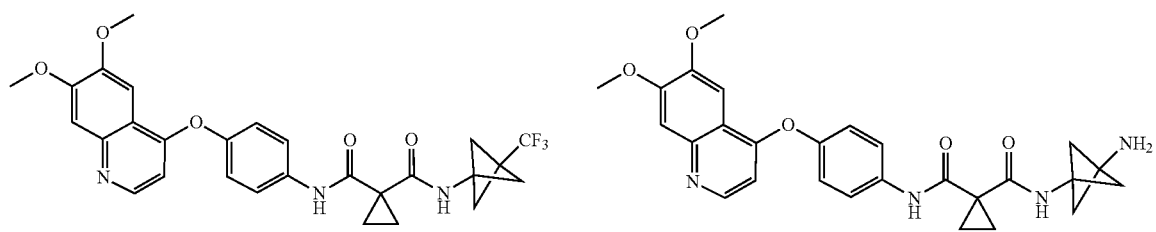
11
12
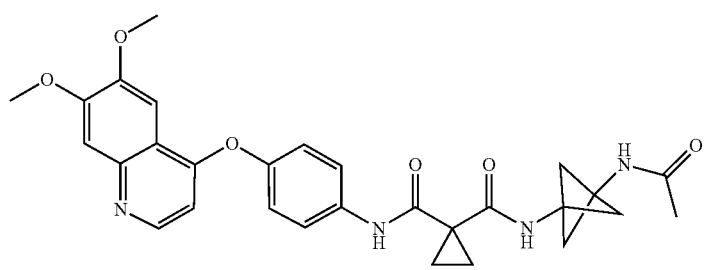
13
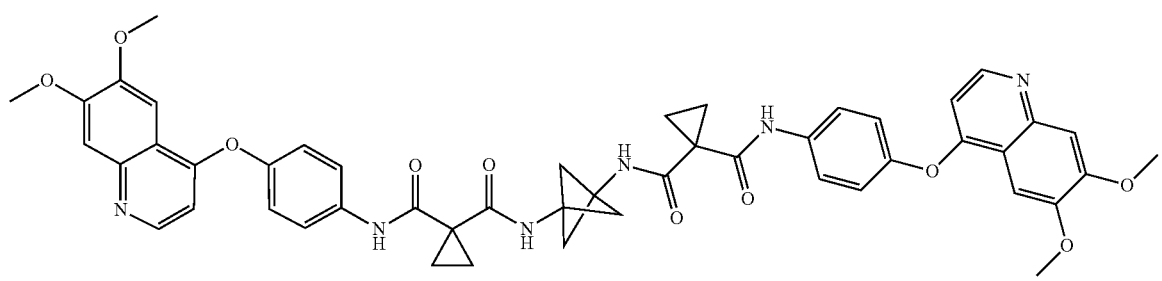
14
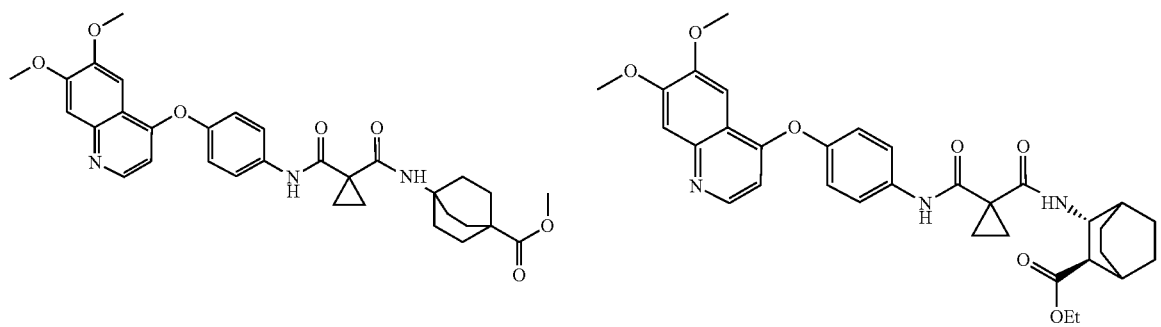
15
16

-continued
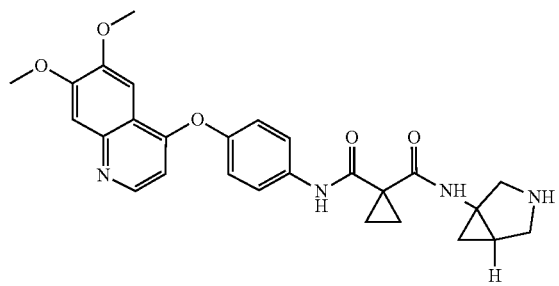
17
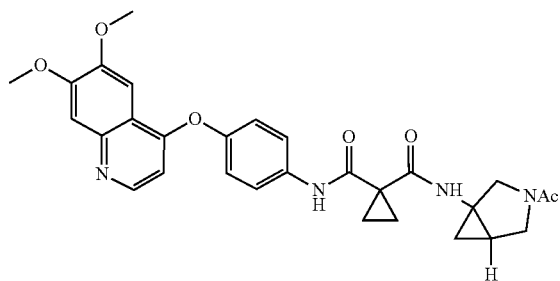
18
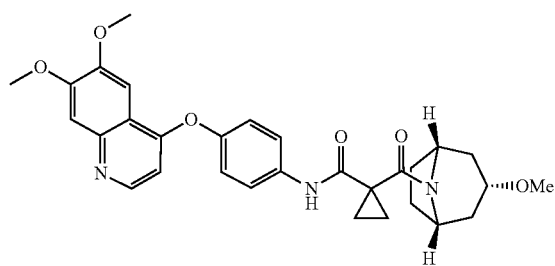
19
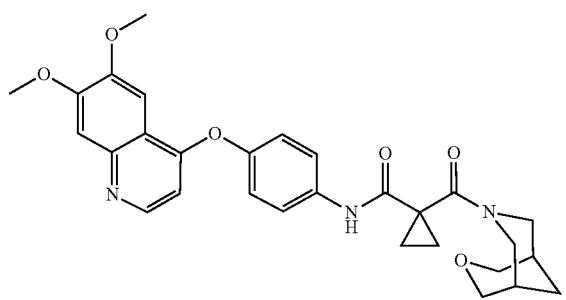
20
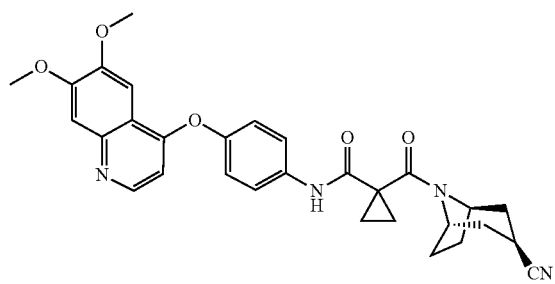
21
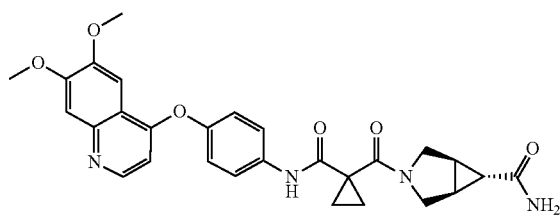
22
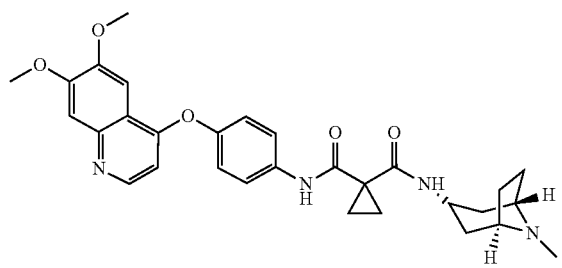
23
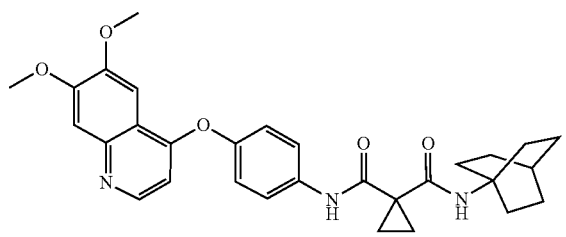
24
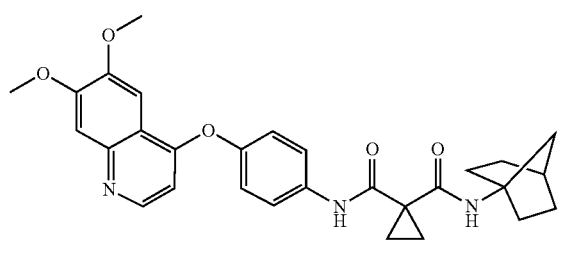
25
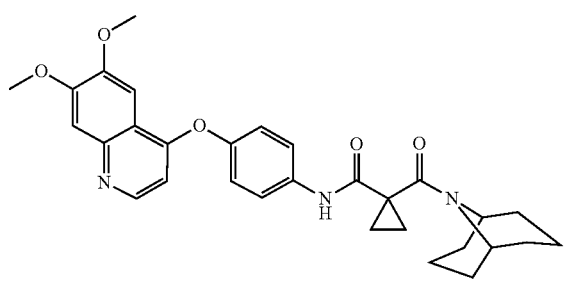
26

-continued
27
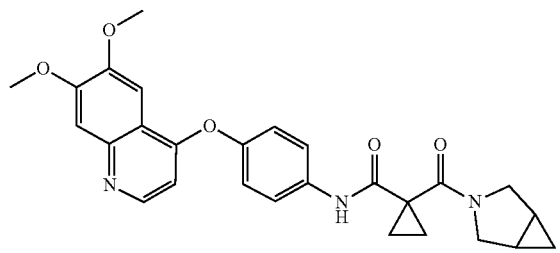
28
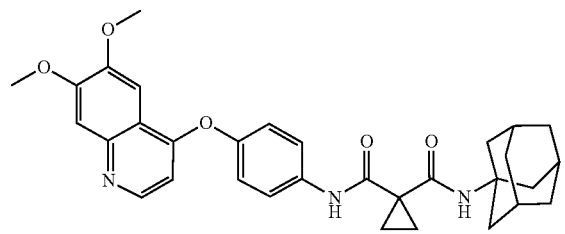
29
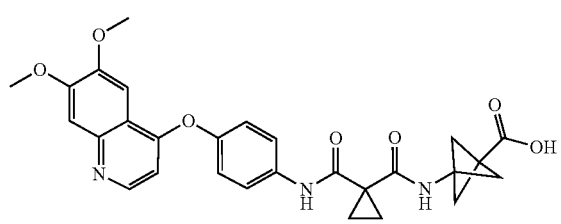
30
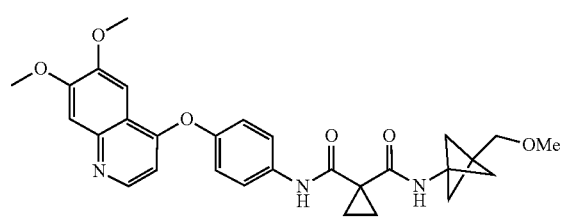
31
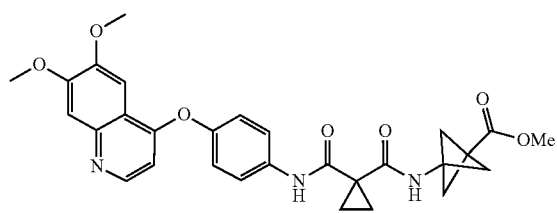
32
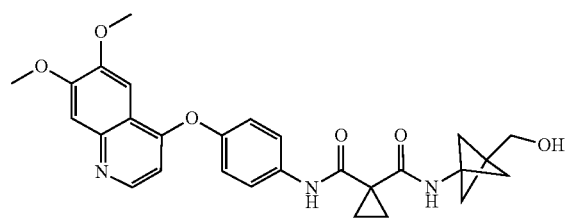
33
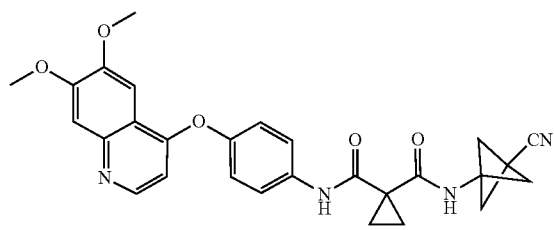
34
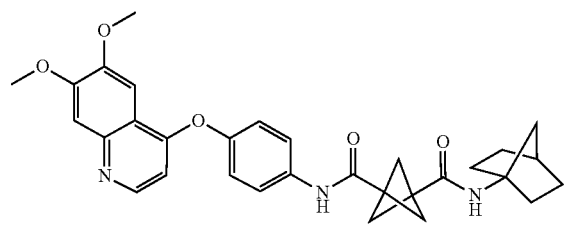
35
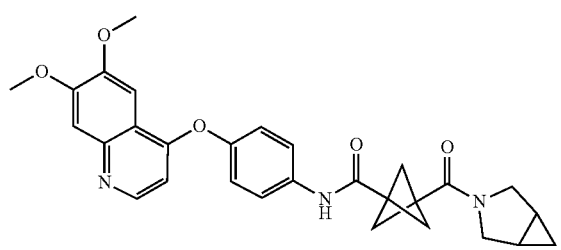
36
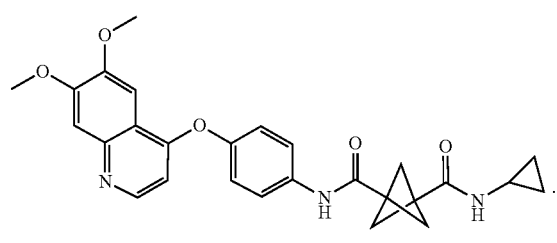

Other embodiments of the present invention includes:

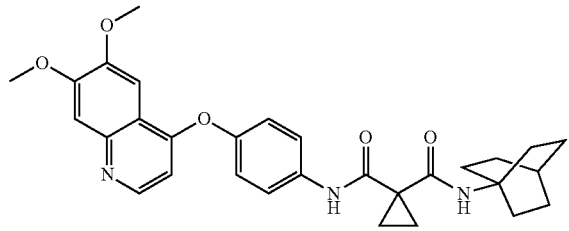

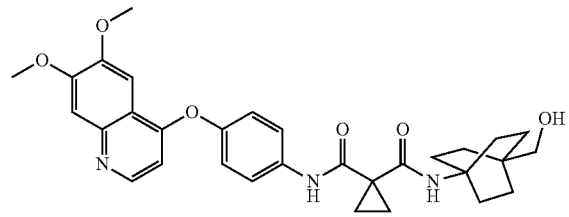

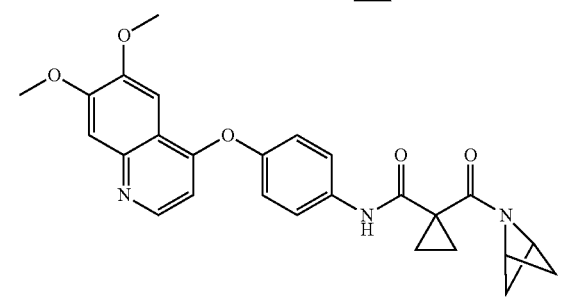

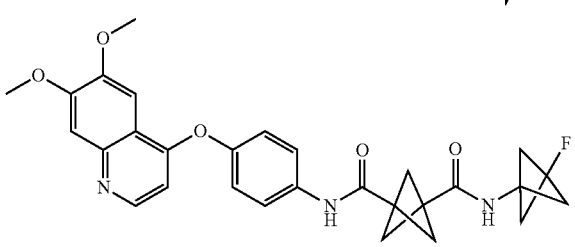

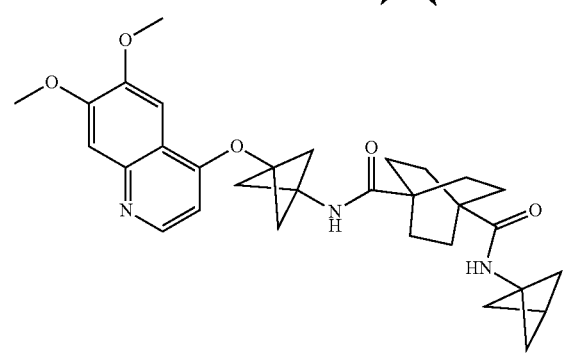

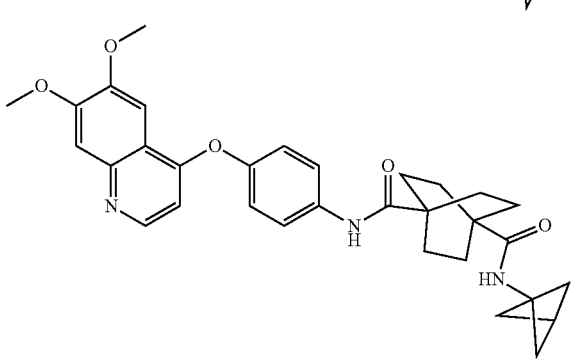

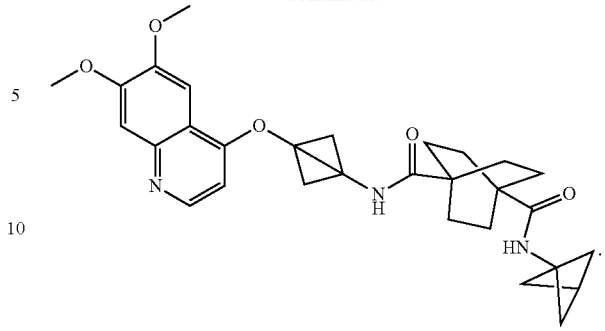

In another aspect, the present invention provides a method of synthesizing a compound of formula (I).

The method includes:
a) coupling a compound of formula (III)

(III)

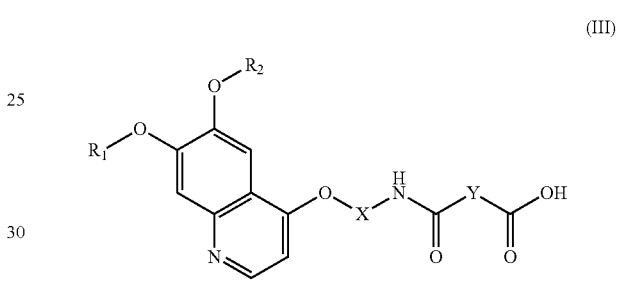

with an amine ZH to form a compound of formula (I); wherein X, Y, Z, $R_1$ and $R_2$ are as defined herein; and wherein at least one of X, Y and Z is an optionally substituted bridged moiety.

In some embodiments, the amine ZH is an amine salt.

In another embodiment, the coupling step is performed in the presence of an amide coupling reagent. The amide coupling reagent can be, but not limited to, 1-[Bis(dimethylamino)methylene]-1H-1,2,3-triazolo[4,5-b]pyridinium 3-oxid hexafluorophosphate (HATU, Hexafluorophosphate Azabenzotriazole Tetramethyl Uronium) and N, N-Diisopropylethylamine (DIPEA, Hünig's base).

The method can further include a step prior to step (a) of:
ia) hydrolysing a compound of formula (IV)

(IV)

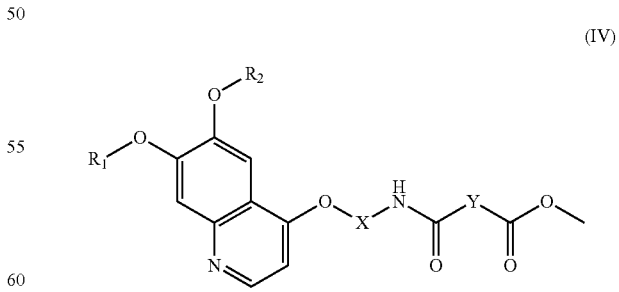

with a base to form a compound of formula (III); wherein X, Y, $R_1$ and $R_2$ are as defined herein.

The base hydrolyses the ester moiety of compound of formula (IV). The base can be, but not limited to, LiOH, NaOH or KOH.

The method can further include a step prior to step (ia) of:
iia) coupling a compound of formula (V)

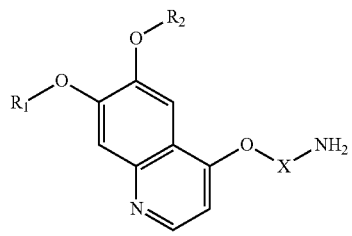

with a compound of formula (VI)

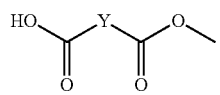

to form a compound of formula (IV);
wherein X, Y, $R_1$ and $R_2$ are as defined herein.

In another embodiment, the coupling step is performed in the presence of an amide coupling reagent. The amide coupling reagent can be, but not limited to, 1-[Bis(dimethylamino)methylene]-1H-1,2,3-triazolo[4,5-b]pyridinium 3-oxid hexafluorophosphate (HATU, Hexafluorophosphate Azabenzotriazole Tetramethyl Uronium) and N, N-Diisopropylethylamine (DIPEA, Hünig's base).

The compounds of the present invention may be for use in therapy.

The compounds of the present invention may be for use in the treatment of cancer.

The present invention discloses a use of a compound of formula (I) or a pharmaceutically acceptable salt, solvate or prodrug thereof in the manufacture of a medicament for treating cancer in a patient in need thereof.

The present invention discloses a method for treating cancer in a patient in need thereof, the method comprising administering to the patient a therapeutically effective amount of a compound of formula (I) or a pharmaceutically acceptable salt, solvate or prodrug thereof.

The cancer may be selected from the group consisting of liver cancer, thyroid cancer, kidney cancer, colorectal cancer, gastrointestinal cancer, skin cancer, lung cancer and bladder cancer. In particular, the cancer may be hepatocellular carcinoma, medullary thyroid cancer, gastrointestinal stromal tumor, urothelial carcinoma, metastatic melanoma, renal cell carcinoma, squamous non-small cell lung cancer, small cell lung cancer and melanoma. It will be understood that the compounds can be used in the treatment of cancer by inhibiting it through modulating cellular kinase activities such as differentiation, chemoinvasion, programmed cell death, proliferation and migration.

The compounds of the present invention may be used as anti-cancer agents, anti-infective agents, immunostimulatory and/or immunomodulatory agents. The compounds of the present invention may also be used as adjunctive agents in combination with chemotherapeutic, radiation or other standard of care for neoplasms.

The compounds of the invention are to be administered to the subject in a treatment effective amount. As used herein, a treatment effective amount is intended to include at least partially attaining the desired effect, or delaying the onset of, or inhibiting the progression of, or halting or reversing altogether the onset or progression of the particular disease of condition being treated.

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage may be in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another preferred embodiment, the dosage may be in the range of 1 mg to 100 mg per kg of body weight per dosage, such as up to 50 mg per body weight per dosage.

Suitable dosage amounts and dosing regimens can be determined by the attending physician and may depend on the particular condition being treated, the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Preferably, the compounds of the present invention may be administered to a subject as a pharmaceutically acceptable salt. It will be appreciated however that non-pharmaceutically acceptable salts also fall within the scope of the present invention since these may be useful as intermediates in the preparation of pharmaceutically acceptable salts. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benzenesulphonic, salicyclic sulphanilic, aspartic, glutamic, edetic, stearic, palmitic, oleic, lauric, pantothenic, tannic, ascorbic and valeric acids.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will be appreciated that any compound that is a prodrug of a compound of formula (I) or (Ia) is also within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free amino group is converted into an amide (eg. α-aminoacid amide). Procedures for esterifying, eg. acylating, the compounds of the invention are well known in the art and may include treatment of the compound with an appropriate carboxylic acid, anhydride or chloride in the presence of a suitable catalyst or base.

The compounds of the invention may be in crystalline form either as the free compounds or as solvates (e.g. hydrates) and it is intended that both forms are within the scope of the present invention. Methods of solvation are generally known within the art.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, eg., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

General Protocol of Compound of Formula (I)

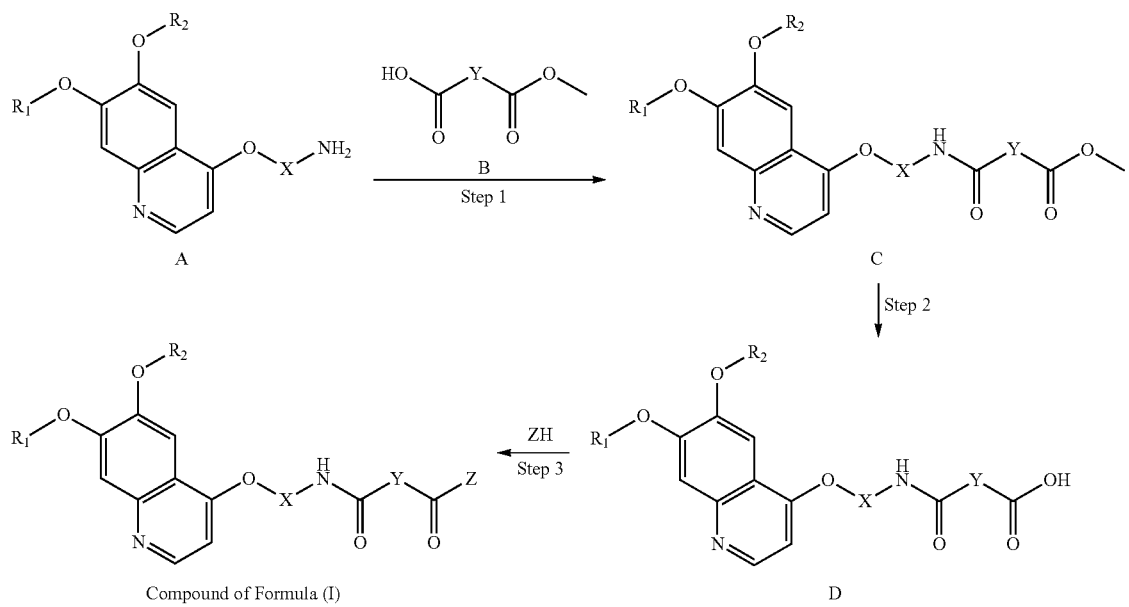

Intermediate B can, for example, be 3-(methoxycarbonyl) bicyclo[1.1.1]pentane-1-carboxylic acid or 1-(methoxycarbonyl)cyclopropanecarboxylic acid. This compound is commercially available from Sigma Aldrich.

Commercially available intermediate ZH can be purchased from Sigma Aldrich. For example, amine salts such as aniline hydrochloride, hydroxymethyl-1-cyclohexylamine hydrochloride and 2-(trifluoromethyl)piperidine hydrochloride are commercially available. Bridged cycloalkane derivatives such as 1-aminobicyclo[1.1.1]pentane, or 3-fluorobicyclo[1.1.1]pentan-1-amine can be synthesized using the following protocols, which are incorporated herein by references (Org. Lett. 2014, 16, 1884-1887 and Org. and Biomol. Chem. 2015, 13, 11597 respectively). 3-phenylbicyclo[1.1.1]pentane-1-amine can be synthesized following the protocol reported in Chem. Comm. 2015, 51, 3139 and 3-(pyrazin-2-yl)bicyclo[1.1.1]pentan-1-amine can be synthesized by employing procedure reported in Org. and Biomol. Chem. 2016, 14, 9485, which are incorporated herein by references.

1-aminobicyclo[1.1.1]pentane

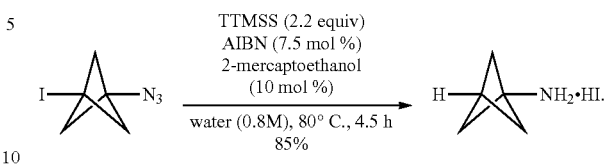

Briefly, to a heterogeneous mixture of 1-azido-3-iodobicyclo[1.1.1]pentane in water was added tris(trimethylsilyl)silane (TTMSS) and the resulting mixture was stirred for 10 min, during which a gentle exotherm was observed. 2-mercaptoethanol followed by azobisisobutyronitrile (AIBN) were added and stirred for another 10 min. The reaction mixture was heated at 80° C. and stirred for 4.5 h, during which an additional identical amount of AIBN was added at 1.5 h and 3 h interval. The reaction mixture was allowed to cool to room temperature, rinsed out with a small amount of ethyl acetate (EtOAc) and water, and the aqueous layer collected. The organic layer was washed with water, and the combined aqueous extracts washed with dichloromethane (DCM), EtOAc, then fully evaporated to dryness. The yellow residue obtained was washed with EtOAc, then filtered and dried in vacuo to afford bicyclo[1.1.1]pentan-1-amine hydroiodide as an off-white powder. The EtOAc washings were evaporated and the residue washed with EtOAc to give a second crop of the bicyclo[1.1.1]pentan-1-amine hydroiodide as an off-white powder.

3-fluorobicyclo[1.1.1]pentan-1-amine

To 3-(methoxycarbonyl)bicyclo[1.1.1]pentane-1-carboxylic acid was added AgNO₃ and SELECTFLUOR®, was thoroughly flushed with argon under a condenser. To this mixture was added deoxygenated water and stirred at 65° C. for 16 h. The reaction was allowed to cool to room temperature (rt) and extracted with diethyl ether. To this ether extract was added NaOH dissolved in 3:1 tetrahydrofuran (THF):water, forming a biphasic reaction mixture. This mixture was stirred at 50° C. for 16 h. The reaction was allowed to cool to rt, and the organic layer separated. The aqueous layer was acidified with 2 N HCl and extracted with diethyl ether, dried over sodium sulphate, filtered and evaporated to dryness. This solid was re-dissolved in pentane and filtered slowly. The filtrate was concentrated in vacuo to afford 3-fluorobicyclo[1.1.1]pentane-1-carboxylic acid as a white solid.

To a dried reaction vessel was added 3-fluorobicyclo[1.1.1]pentane-1-carboxylic acid, was thoroughly flushed with argon under a condenser. Anhydrous t-BuOH followed by triethylamine were added. Diphenylphosphoryl azide was added dropwise into the reaction mixture within 15 min and stirred at rt for 2 h, followed by refluxing for another 3 h. The reaction mixture was evaporated under reduced pressure and diluted with diethyl ether. This ether extract was washed with saturated bicarbonate, dried over sodium sulphate, filtered and concentrated in vacuo. The residue was purified by silica gel flash chromatography to afford tert-butyl (3-fluorobicyclo[1.1.1]pentan-1-yl)carbamate as a white solid.

To tert-butyl (3-fluorobicyclo[1.1.1]pentan-1-yl)carbamate was added 4 N HCl in dioxane and stirred overnight at rt. Reaction mixture was then evaporated to dryness to furnish the crude product as a pale yellow solid. This residue was then washed with diethyl ether followed by DCM, to afford 3-fluorobicyclo[1.1.1]pentan-1-aminium chloride as a white solid.

Synthesis of intermediate C (Step 1): The compound A (1.0 eq.) was added to a stirred solution of HATU (1.05 eq.), acid B (1.0 eq.) and DIPEA (1.5 eq.) in DMF and the mixture was stirred at room temperature (RT) for 2 hrs. After complete consumption of A, as monitored by LCMS/TLC, reaction mixture was diluted with water. The resulting solution was extracted in EtOAc. The combined organic extract was dried over anhydrous Na₂SO₄ and concentrated on rotary evaporator. The residue was triturated in diethyl ether to afford compound C.

Synthesis of scaffold intermediate D (step 2): LiOH monohydrate (4.0 eq.) was added to a solution of compound C (1.0 eq.) in mixture of methanol & THF at RT and the mixture was stirred at same temperature for 16 hrs. After consumption of C, as monitored by LCMS/TLC, reaction mixture concentrated on rotary evaporator. The resulting residue was diluted with water followed by 1N HCl (pH ~3). The resulting solid was filtered and vacuum dried to afford compound D.

Synthesis of compound of Formula (I) (step 3): The salt form of amine ZH (1.1 eq.) was added to a stirred solution of HATU (1.05 eq.), compound D (1.0 eq.) and DIPEA (4.0 eq.) in DMF at RT and the mixture was stirred at same temperature for 2 hrs. After complete consumption of D, as monitored by LCMS/TLC, reaction mixture was concentrated and the residue was diluted with water. The resulting suspension was extracted in EtOAc. The combined organic extract was dried over anhydrous Na₂SO₄ and concentrated on rotary evaporator. The residue was purified by silica gel flash column chromatography using MeOH/DCM mixture to afford compound of Formula (I). In some examples, the compound is an off-white solid.

Compounds 1 to 36 as depicted herein were prepared be the above protocol.

Exemplary Synthesis of Compound 9

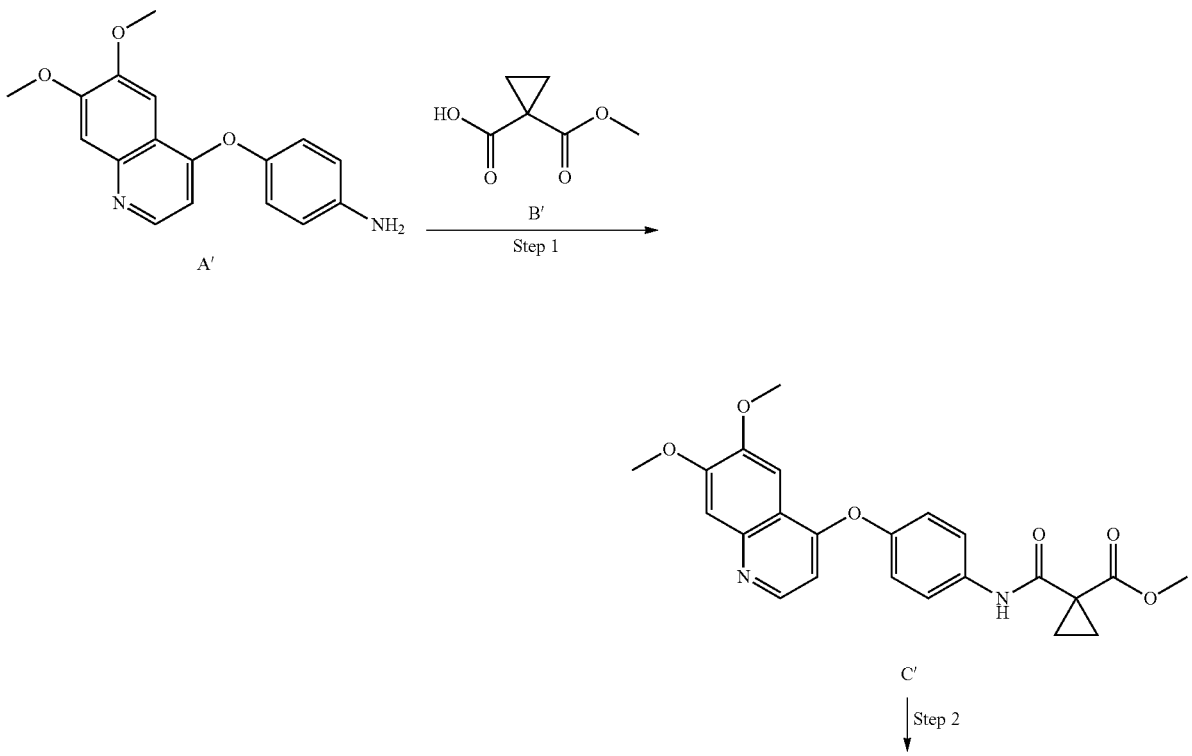

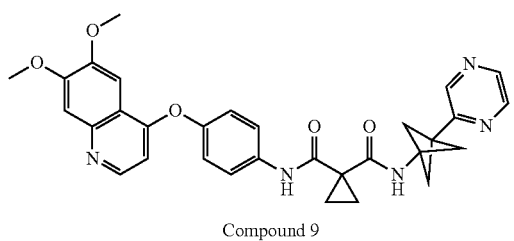 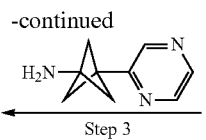 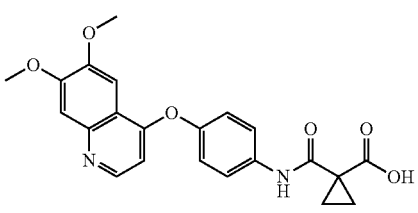

Compound 9                                      Step 3                                      D'

4-[(6,7-Dimethoxyquinolin-4-yl)oxy]aniline (1.0 eq.; A') was added to a stirred solution of HATU (1.05 eq.), 1-(methoxycarbonyl)cyclopropanecarboxylic acid (1.0 eq.; B') and DIPEA (1.5 eq.) in DMF and the mixture was stirred at room temperature (RT) for 2 hrs. After complete consumption of the aniline, as monitored by LCMS/TLC, reaction mixture was diluted with water. The resulting solution was extracted in EtOAc. The combined organic extract was dried over anhydrous $Na_2SO_4$ and concentrated on rotary evaporator. The residue was triturated in diethyl ether to afford compound C'.

LiOH monohydrate (4.0 eq.) was added to a solution of compound C' (1.0 eq.) in mixture of methanol & THF at RT and the mixture was stirred at same temperature for 16 hrs. After consumption of C', as monitored by LCMS/TLC, reaction mixture concentrated on rotary evaporator. The resulting residue was diluted with water followed by 1N HCl (pH ~3). The resulting solid was filtered and vacuum dried to afford compound D'.

3-(pyrazin-2-yl)bicyclo[1.1.1]pentan-1-amine (1.1 eq.) was added to a stirred solution of HATU (1.05 eq.), compound D' (1.0 eq.) and DIPEA (4.0 eq.) in DMF at RT and the mixture was stirred at same temperature for 2 hrs. After complete consumption of D', as monitored by LCMS/TLC, reaction mixture was concentrated and the residue was diluted with water. The resulting suspension was extracted in EtOAc. The combined organic extract was dried over anhydrous $Na_2SO_4$ and concentrated on rotary evaporator. The residue was purified by silica gel flash column chromatography using MeOH/DCM mixture to afford compound 9 as an off-white solid.

Compound Characterization

N-(bicyclo[1.1.1]pentan-1-yl)-N-(4-(6,7-dimethoxyquinolin-4-yloxy)phenyl)cyclopropane-1,1-dicarboxamide (1)

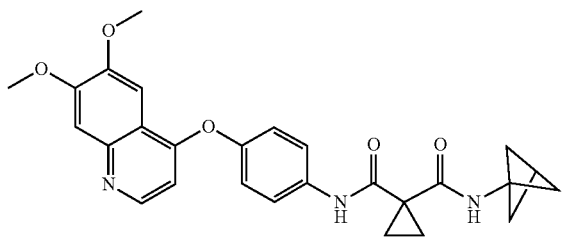 [SMILES: COc1cc2nccc(Oc3ccc(NC(=O)C4(C(=O)NC56CC(C5)C6)CC4)cc3)c2cc1OC]

$^1$HNMR (400 MHz, DMSO-d6): δ 10.67 (brs, 1H), 8.44 (d, J=4.8 Hz, 1H), 8.36 (s, 1H), 7.70 (d, J=8.4 Hz, 2H), 7.47 (s, 1H), 7.36 (s, 1H), 7.19 (d, J=8.4 Hz, 2H), 6.40 (d, J=4.4 Hz, 1H), 3.91 (s, 3H), 3.90 (s, 3H), 1.98 (s, 6H), 1.33 (m, 4H). (Signal expected from BCP skeleton was found merged with signal resulting from residual DMSO-d6). $^1$H NMR (400 MHz, $CD_2Cl_2$) δ 10.74 (brs, 1H), 8.44 (d, J=5.2 Hz, 1H), 7.67-7.65 (m, 2H), 7.56 (s, 1H), 7.38 (s, 1H), 7.16-7.14 (m, 2H), 6.46 (d, J=5.2 Hz, 1H), 6.24 (brs, 1H), 4.00 (d, J=5.4 Hz, 6H), 2.47 (s, 1H), 2.10 (s, 6H), 1.70-1.64 (m, 2H), 1.33-1.28 (m, 2H).

$^{13}$CNMR (101 MHz, DMSO-d6): δ 171.4, 168.6, 160.5, 153.1, 149.9, 149.8, 149.1, 146.7, 136.6, 122.2, 121.6, 115.6, 108.2, 103.5, 99.6, 56.2, 52.8, 49.2, 29.9, 24.9, 16.4. $^{13}$C NMR (101 MHz, $CD_2Cl_2$): δ 173.1, 168.4, 161.2, 153.6, 151.1, 150.3, 149.4, 147.6, 136.3, 122.4, 121.9, 116.6, 108.5, 103.9, 100.1, 56.6, 53.2, 49.16, 28.5, 25.4, 18.1.

ES-MS [m+H]+: m/z 474.1.

LC-MS analysis t$^R$: 4.19 min (Method: Column: Symmetry—C18 4.6×75 mm, 3.5 μm; wavelength: 254 nm; flow: 0.8 mL/min; run time: 12 min; Time & mobile phase-gradient (time in min/B): 0/50, 3/95, 9/95, 10/50, 12/50 [B: Acetonitrile; A: Ammonium formate (20 mmol in water)]; LC—Agilent technologies-1260 Infinity II Series; MASS: Agilent technologies-6120 Quadrupole LC/MS-API-ESI.)

N-(4-((6,7-dimethoxyquinolin-4-yl)oxy)phenyl)-N-(3-phenylbicyclo[1.1.1]pentan-1-yl)cyclopropane-1,1-dicarboxamide (2)

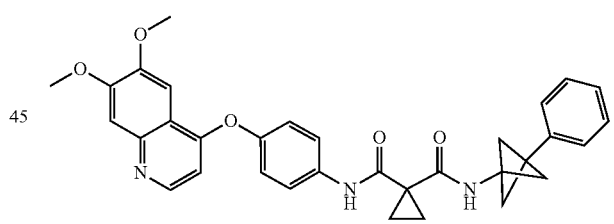

$^1$HNMR (400 MHz, DMSO-d6): δ 10.70 (brs, 1H), 8.48 (s, 1H), 8.44 (d, J=5.2 Hz, 1H), 7.72 (d, J=8.8 Hz, 2H), 7.48 (s, 1H), 7.36 (s, 1H), 7.27 (m, 2H), 7.21-7.19 (m, 5H), 6.40 (d, J=5.2 Hz, 1H), 3.91 (s, 3H), 3.90 (s, 3H), 2.25 (s, 6H), 1.37 (s, 4H).

$^{13}$CNMR (101 MHz, DMSO-d6): δ 171.6, 168.5, 160.5, 153.0, 149.8, 149.7, 149.2, 146.8, 139.6, 136.7, 128.6, 126.9, 126.7, 122.2, 121.7, 115.6, 108.2, 103.4, 99.5, 56.1, 54.8, 45.6, 30.2, 22.2, 16.4.

ES-MS [m+H]$^+$: m/z 550.2.

LC-MS analysis t$^R$: 4.76 min (Method: Column: Symmetry—C18 4.6×75 mm, 3.5 μm; wavelength: 254 nm; flow: 0.8 mL/min; run time: 12 min; Time & mobile phase-gradient (time in min/B): 0/50, 3/95, 9/95, 10/50, 12/50 [B: Acetonitrile; A: Ammonium formate (20 mmol in water)]; LC—Agilent technologies-1260 Infinity II Series; MASS: Agilent technologies-6120 Quadrupole LC/MS-API-ESI.)

N¹-(4-((6,7-dimethoxyquinolin-4-yl)oxy)phenyl)-N3-(3-fluorobicyclo[1.1.1]pentan-1-yl)bicyclo[1.1.1]pentane-1,3-dicarboxamide (3)

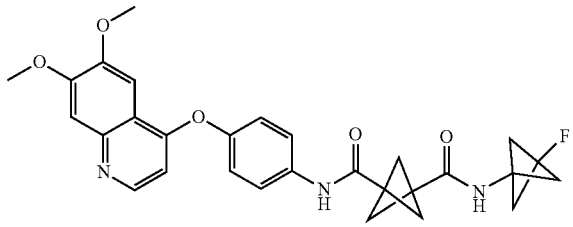 [SMILES: COc1cc2nccc(Oc3ccc(NC(=O)C45CC(C(=O)NC67CC(F)(C6)C7)(C4)C5)cc3)c2cc1OC]

¹HNMR (400 MHz, DMSO-d6): δ 9.73 (s, 1H), 8.56 (s, 1H), 8.44 (d, J=5.2 Hz, 1H), 7.75 (d, J=8.8 Hz, 2H), 7.47 (s, 1H), 7.36 (s, 1H), 7.19 (d, J=8.4 Hz, 2H), 6.40 (d, J=4.8 Hz, 1H), 3.91 (d, 3H), 3.89 (s, 3H), 2.29 (s, 6H), 2.18 (s, 6H).

¹³CNMR (101 MHz, DMSO-d6): δ 170.0, 168.2, 160.4, 153.0, 149.8, 149.7, 149.2, 146.8, 136.6, 122.0, 121.6, 115.6, 108.2, 103.5, 99.5, 77.1 (d, J (C, F)=316.3 Hz), 56.1, 55.2 (d, J (C, F)=20.7 Hz), 52.1, 39.2, 38.7 (d, J (C, F)=35.3 Hz) (signals expected from one of the 4° carbons of BCP skeleton was found merged with that resulting from residual DMSO-d6).

ES-MS [m+H]⁺: m/z 518.1

LC-MS analysis t^R: 3.51 min (Method: Column: Symmetry—C18 4.6×75 mm, 3.5 μm; wavelength: 254 nm; flow: 0.8 mL/min; run time: 12 min; Time & mobile phase-gradient (time in min/B): 0/50, 3/95, 9/95, 10/50, 12/50 [B: Acetonitrile; A: Ammonium formate (20 mmol in water)]; LC—Agilent technologies-1260 Infinity II Series; MASS: Agilent technologies-6120 Quadrupole LC/MS-API-ESI.)

N-(4-((6,7-dimethoxyquinolin-4-yl)oxy)phenyl)-N-(3-fluorobicyclo[1.1.1]pentan-1-yl)cyclopropane-1,1-dicarboxamide (4)

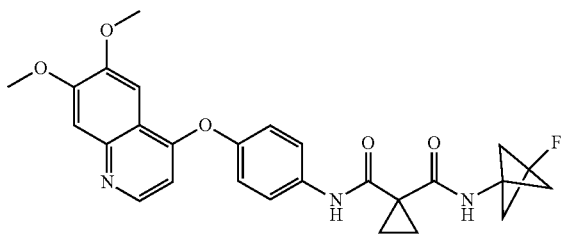 [SMILES: COc1cc2nccc(Oc3ccc(NC(=O)C4(C(=O)NC56CC(F)(C5)C6)CC4)cc3)c2cc1OC]

¹HNMR (400 MHz, DMSO-d6): δ 10.50 (brs, 1H), 8.55 (s, 1H), 8.44 (d, J=5.6 Hz, 1H), 7.71 (d, J=9.2 Hz, 2H), 7.47 (s, 1H), 7.36 (s, 1H), 7.19 (d, J=9.2 Hz, 2H), 6.39 (d, J=5.2 Hz, 1H), 3.91 (s, 3H), 3.90 (s, 3H), 2.30 (d, J (C, F)=2.0 Hz, 6H), 1.34-1.32 (m, 4H).

¹³CNMR (101 MHz, DMSO-d6): δ 171.6, 168.3, 160.4, 153.0, 149.9, 149.8, 149.2, 146.9, 136.7, 122.3, 121.6, 115.6, 108.3, 103.5, 99.6, 77.2 (d, J (C, F)=317.3 Hz), 56.1, 55.3 (d, J (C, F)=19.6 Hz), 30.6, 16.2. (signal expected from one of the 4° carbons of BCP skeleton was found merged with that resulting from residual DMSO-d6).

ES-MS [m+H]⁺: m/z 492.1.

LC-MS analysis t^R: 4.02 min (Method: Column: Symmetry—C18 4.6×75 mm, 3.5 μm; wavelength: 254 nm; flow: 0.8 mL/min; run time: 12 min; Time & mobile phase-gradient (time in min/B): 0/50, 3/95, 9/95, 10/50, 12/50 [B: Acetonitrile; A: Ammonium formate (20 mmol in water)]; LC—Agilent technologies-1260 Infinity II Series; MASS: Agilent technologies-6120 Quadrupole LC/MS-API-ESI.)

3-(1-((4-((6,7-dimethoxyquinolin-4-yl)oxy)phenyl)carbamoyl)cyclopropane-1-carboxamido)bicyclo[1.1.1]pentan-1-yl benzoate (5)

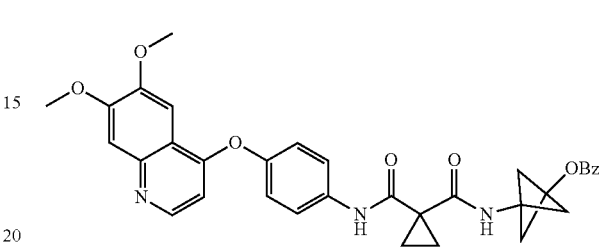

¹H NMR (400 MHz, 10% CD₂Cl₂ in CD₃OD) δ 8.40 (d, J=5.4 Hz, 1H), 8.04-7.94 (m, 2H), 7.74-7.66 (m, 2H), 7.65-7.56 (m, 2H), 7.46 (t, J=7.7 Hz, 2H), 7.35 (s, 1H), 7.24-7.15 (m, 2H), 6.52 (d, J=5.4 Hz, 1H), 4.02 (s, 3H), 4.00 (s, 3H), 2.59 (s, 6H), 1.65-1.57 (m, 2H), 1.54-1.46 (m, 2H).

¹³C NMR (101 MHz, 10% CD₂Cl₂ in CD₃OD) δ 174.2, 170.4, 167.0, 162.5, 154.6, 151.6, 151.1, 149.3, 147.2, 136.9, 134.3, 130.9, 130.4, 129.4, 123.5, 122.4, 117.2, 107.4, 104.2, 100.5, 64.8, 56.5, 56.5, 56.1, 44.1, 29.6, 17.9.

HRMS: (ESI TOF) m/z: [M+H]⁺ Calcd for C₃₄H₃₂N₃O₇ m/z 594.2235; Found 594.2235.

IR: 3447, 2924, 1727, 1669, 1507, 1480, 1432, 1230, 851, 708 cm⁻¹.

N-(4-((6,7-dimethoxyquinolin-4-yl)oxy)phenyl)-N-(3-hydroxybicyclo[1.1.1]pentan-1-yl)cyclopropane-1,1-dicarboxamide (6)

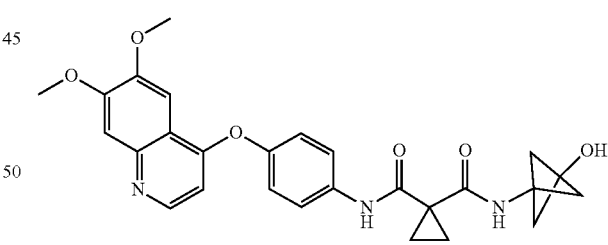

¹H NMR (400 MHz, 10% CD₂Cl₂ in CD₃OD) δ 8.39 (d, J=5.4 Hz, 1H), 7.70-7.63 (m, 2H), 7.61 (s, 1H), 7.34 (s, 1H), 7.21-7.13 (m, 2H), 6.50 (d, J=5.4 Hz, 1H), 4.02 (s, 3H), 4.00 (s, 3H), 2.18 (s, 6H), 1.62-1.55 (m, 2H), 1.50-1.42 (m, 2H).

¹³C NMR (101 MHz, 10% CD₂Cl₂ in CD₃OD) δ 173.8, 170.3, 162.2, 154.3, 151.3, 150.8, 149.1, 147.0, 136.6, 123.3, 122.2, 117.0, 107.3, 104.0, 100.4, 62.8, 56.5, 56.4, 56.1, 41.9, 29.2, 17.8.

HRMS: (ESI TOF) m/z: [M+H]⁺ Calcd for C₂₇H₂₈N₃O₆ m/z 490.1973; Found 490.1969.

IR: 3341, 2919, 1663, 1407, 1481, 1432, 1254, 1217, 852 cm⁻¹.

N-(3-carbamoylbicyclo[1.1.1]pentan-1-yl)-N-(4-((6,7-dimethoxyquinolin-4-yl)oxy)phenyl)cyclopropane-1,1-dicarboxamide (7)

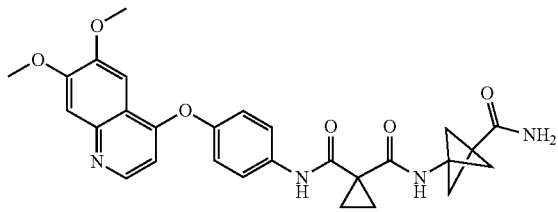 [SMILES: COc1cc2nccc(Oc3ccc(NC(=O)C4(C(=O)NC56CC(C(N)=O)(C5)C6)CC4)cc3)c2cc1OC]

$^1$H NMR (400 MHz, 10% CD$_2$Cl$_2$ in CD$_3$OD) δ 8.39 (d, J=5.4 Hz, 1H), 7.71-7.64 (m, 2H), 7.61 (s, 1H), 7.35 (s, 1H), 7.22-7.15 (m, 2H), 6.51 (d, J=5.4 Hz, 1H), 4.02 (s, 3H), 4.00 (s, 3H), 2.33 (s, 6H), 1.63-1.56 (m, 2H), 1.50-1.44 (m, 2H).

$^{13}$C NMR (101 MHz, 10% CD$_2$Cl$_2$ in CD$_3$OD) δ 174.6, 174.2, 170.4, 162.4, 154.5, 151.5, 151.0, 149.3, 147.2, 136.8, 123.5, 122.3, 117.2, 107.4, 104.1, 100.5, 56.5, 56.5, 46.0, 38.1, 29.4, 17.9. One of the peaks is hidden inside CD$_2$Cl$_2$.

HRMS: (ESI TOF) m/z: [M+H]$^+$ Calcd for C$_{28}$H$_{29}$N$_4$O$_6$ m/z 517.2082; Found 517.2078.

IR: 3338, 2965, 2383, 1654, 1508, 1491, 1432, 1351, 1256, 1217, 851, 815, 750 cm$^{-1}$.

N-(4-((6,7-dimethoxyquinolin-4-yl)oxy)phenyl)-N-(3-(dimethylcarbamoyl)bicyclo[1.1.1]pentan-1-yl)cyclopropane-1,1-dicarboxamide (8)

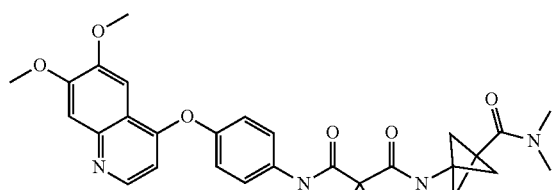

$^1$H NMR (400 MHz, 10% CD$_2$Cl$_2$ in CD$_3$OD) δ 8.39 (d, J=5.4 Hz, 1H), 7.72-7.65 (m, 2H), 7.61 (s, 1H), 7.35 (s, 1H), 7.23-7.15 (m, 2H), 6.51 (d, J=5.4 Hz, 1H), 4.02 (s, 3H), 4.00 (s, 3H), 3.13 (s, 3H), 2.93 (s, 3H), 2.44 (s, 6H), 1.63-1.56 (m, 2H), 1.50-1.44 (m, 2H).

$^{13}$C NMR (101 MHz, 10% CD$_2$Cl$_2$ in CD$_3$OD) δ 174.3, 170.9, 170.4, 162.5, 154.6, 151.6, 151.1, 149.3, 147.2, 136.9, 123.5, 122.4, 117.2, 107.4, 104.2, 100.5, 56.5, 56.5, 55.8, 47.4, 39.0, 38.0, 36.5, 29.5.

HRMS: (ESI TOF) m/z: [M+H]$^+$ Calcd for C$_{30}$H$_{33}$N$_4$O$_6$ m/z 545.2395; Found 545.2392.

IR: 3406, 2924, 1617, 1507, 1480, 1251, 1217, 1169, 995, 853 cm$^{-1}$.

N-(4-((6,7-dimethoxyquinolin-4-yl)oxy)phenyl)-N-(3-(pyrazin-2-yl)bicyclo[1.1.1]pentan-1-yl)cyclopropane-1,1-dicarboxamide (9)

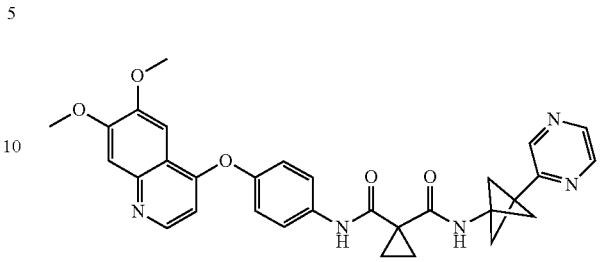

$^1$H NMR (400 MHz, 10% CD$_2$Cl$_2$ in CD$_3$OD) δ 8.56 (d, J=1.6 Hz, 1H), 8.53 (dd, J=2.6, 1.6 Hz, 1H), 8.47 (d, J=2.6 Hz, 1H), 8.41 (d, J=5.4 Hz, 1H), 7.75-7.68 (m, 2H), 7.62 (s, 1H), 7.36 (s, 1H), 7.25-7.16 (m, 2H), 6.53 (d, J=5.4 Hz, 1H), 4.02 (s, 3H), 4.00 (s, 3H), 2.52 (s, 6H), 1.64-1.57 (m, 2H), 1.54-1.46 (m, 2H).

$^{13}$C NMR (101 MHz, 10% CD$_2$Cl$_2$ in CD$_3$OD) δ 174.3, 170.6, 162.6, 155.2, 154.8, 151.7, 151.2, 149.4, 147.4, 145.1, 143.9, 143.8, 137.1, 123.6, 122.4, 117.3, 107.5, 104.2, 100.6, 56.5, 56.5, 55.6, 47.0, 39.8, 29.8, 17.8.

HRMS: (ESI TOF) m/z: [M+H]$^+$ Calcd for C$_{31}$H$_{30}$N$_5$O$_5$ m/z 552.2242; Found 552.2241.

IR: 3501, 3275, 2931, 1673, 1506, 1480, 1252, 1216, 852 cm$^{-1}$.

N-(4-((6,7-dimethoxyquinolin-4-yl)oxy)phenyl)-N-(3-methylbicyclo[1.1.1]pentan-1-yl)cyclopropane-1,1-dicarboxamide (10)

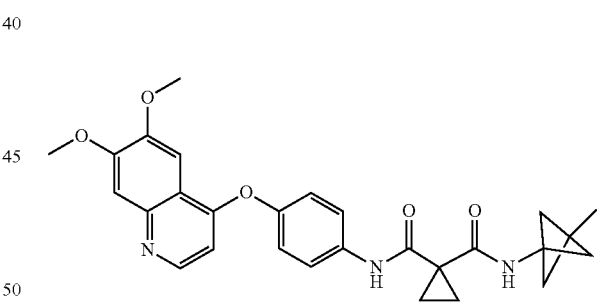

$^1$H NMR (400 MHz, 10% CD$_2$Cl$_2$ in CD$_3$OD) δ 8.39 (d, J=5.4 Hz, 1H), 7.68 (d, J=8.5 Hz, 2H), 7.61 (s, 1H), 7.35 (s, 1H), 7.19 (d, J=8.5 Hz, 2H), 6.51 (d, J=5.4 Hz, 1H), 4.02 (s, 3H), 4.00 (s, 3H), 1.95 (s, 6H), 1.62-1.54 (m, 2H), 1.49-1.41 (m, 2H), 1.22 (s, 3H).

$^{13}$C NMR (101 MHz, 10% CD$_2$Cl$_2$ in CD$_3$OD) δ 173.8, 170.6, 162.5, 154.5, 151.5, 151.0, 149.3, 147.1, 136.8, 123.5, 122.3, 117.2, 107.3, 104.1, 100.5, 56.5, 56.5, 55.1, 46.2, 34.9, 29.4, 17.7, 16.6.

HRMS: (ESI TOF) m/z: [M+H]$^+$ Calcd for C$_{28}$H$_{30}$N$_3$O$_5$ m/z 488.2180; Found 488.2181.

IR: 3569, 2963, 1679, 1507, 1481, 1218, 772 cm$^{-1}$.

N-(4-((6,7-dimethoxyquinolin-4-yl)oxy)phenyl)-N-(3-(trifluoromethyl)bicyclo[1.1.1]pentan-1-yl)cyclopropane-1,1-dicarboxamide (11)

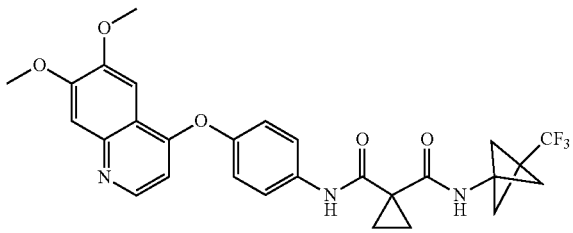 [SMILES: COc1cc2nccc(Oc3ccc(NC(=O)C4(C(=O)NC56CC(C(F)(F)F)(C5)C6)CC4)cc3)c2cc1OC]

$^1$H NMR (400 MHz, 10% CD$_2$Cl$_2$ in CD$_3$OD) δ 8.40 (d, J=5.4 Hz, 1H), 8.00-7.65 (m, 2H), 7.62 (s, 1H), 7.35 (s, 1H), 7.23-7.04 (m, 2H), 6.51 (d, J=5.4 Hz, 1H), 4.02 (s, 3H), 4.00 (s, 3H), 2.31 (s, 6H), 1.65-1.57 (m, 2H), 1.52-1.43 (m, 2H).
$^{13}$C NMR (101 MHz, 10% CD$_2$Cl$_2$ in CD$_3$OD) δ 174.4, 170.3, 162.6, 154.6, 151.6, 151.1, 149.3, 147.2, 137.0, 123.6, 122.4, 117.2, 107.4, 104.2, 100.5, 56.5, 56.5, 52.2, 46.5, 37.76-34.76 (m, J$_{C-F}$), 29.6, 17.9. CF$_3$ carbon is too small to be observed.
$^{19}$F NMR (376 MHz, 10% CD$_2$Cl$_2$ in CD$_3$OD) δ−68.9.
HRMS: (ESI TOF) m/z: [M+H]$^+$ Calcd for C$_{28}$H$_{27}$F$_3$N$_3$O$_5$ m/z 542.1898; Found 542.1896.
IR: 3252, 1672, 1526, 1507, 1483, 1218, 1170, 1127, 852, 771 cm$^{-1}$.

N-(3-aminobicyclo[1.1.1]pentan-1-yl)-N-(4-((6,7-dimethoxyquinolin-4-yl)oxy)phenyl)cyclopropane-1,1-dicarboxamide (12)

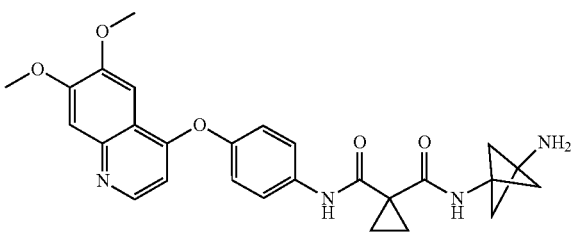 [SMILES: COc1cc2nccc(Oc3ccc(NC(=O)C4(C(=O)NC56CC(N)(C5)C6)CC4)cc3)c2cc1OC]

$^1$H NMR (400 MHz, 10% CD$_2$Cl$_2$ in CD$_3$OD) δ 8.40 (d, J=5.4 Hz, 1H), 7.74-7.66 (m, 2H), 7.62 (s, 1H), 7.35 (s, 1H), 7.24-7.17 (m, 2H), 6.52 (d, J=5.4 Hz, 1H), 4.02 (s, 3H), 4.00 (s, 3H), 2.11 (s, 6H), 1.60-1.52 (m, 2H), 1.49-1.41 (m, 2H).
$^{13}$C NMR (101 MHz, 10% CD$_2$Cl$_2$ in CD$_3$OD) δ 174.0, 170.7, 162.7, 154.8, 151.7, 151.3, 149.5, 147.4, 137.2, 123.6, 122.5, 117.3, 107.5, 104.2, 100.6, 56.5, 56.5, 56.0, 44.0, 30.0, 17.6. 1 tertiary C of BCP moiety inside CD3OD; verified by HMBC.
HRMS: (ESI TOF) m/z: [M+H]$^+$ Calcd for C$_{27}$H$_{29}$N$_4$O$_5$ m/z 489.2133; Found 489.2131.
IR: 3297, 2977, 1672, 1506, 1480, 1350, 1269, 1252, 1216, 1168, 995, 853 cm$^{-1}$.

N-(3-acetamidobicyclo[1.1.1]pentan-1-yl)-N-(4-((6,7-dimethoxyquinolin-4-yl)oxy)phenyl)cyclopropane-1,1-dicarboxamide (13)

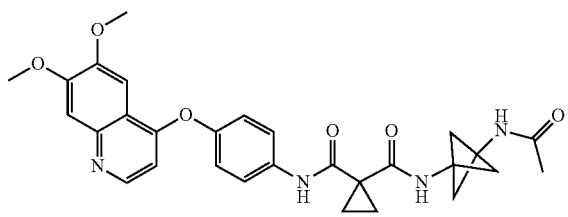 [SMILES: COc1cc2nccc(Oc3ccc(NC(=O)C4(C(=O)NC56CC(NC(C)=O)(C5)C6)CC4)cc3)c2cc1OC]

$^1$H NMR (400 MHz, CD$_3$OD) δ 8.41 (d, J=5.4 Hz, 1H), 7.74-7.67 (m, 2H), 7.62 (s, 1H), 7.35 (s, 1H), 7.24-7.17 (m, 2H), 6.53 (d, J=5.4 Hz, 1H), 4.01 (s, 3H), 4.00 (s, 3H), 2.35 (s, 6H), 1.89 (s, 3H), 1.59-1.52 (m, 2H), 1.49-1.42 (m, 2H).
$^{13}$C NMR (101 MHz, CD$_3$OD) δ 174.1, 173.7, 170.6, 162.8, 154.9, 151.8, 151.4, 149.6, 147.4, 137.3, 123.7, 122.6, 117.4, 107.5, 104.3, 100.6, 56.5, 56.5, 55.7, 46.1, 45.7, 30.1, 22.8, 17.6.
HRMS: (ESI TOF) m/z: [M+H]$^+$ Calcd for C$_{29}$H$_{31}$N$_4$O$_6$ m/z 531.2238; Found 531.2238.
IR: 3277, 3011, 1662, 1506, 1480, 1432, 1350, 1253, 1216, 1169, 996, 854 cm$^{-1}$.

N,N'-(bicyclo[1.1.1]pentane-1,3-diyl)bis(N-(4-((6,7-dimethoxyquinolin-4-yl)oxy)phenyl)cyclopropane-1,1-dicarboxamide) (14)

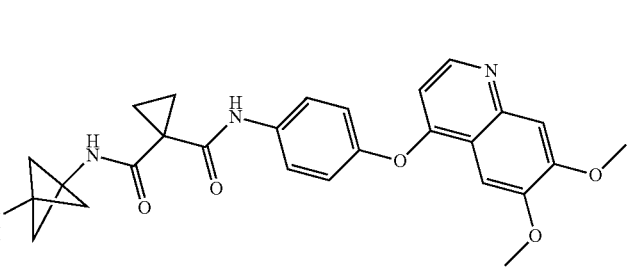

$^1$H NMR (400 MHz, 10% CD$_2$Cl$_2$ in CD$_3$OD) δ 8.39 (d, J=5.4 Hz, 2H), 7.70-7.63 (m, 4H), 7.61 (s, 2H), 7.35 (s, 2H), 7.23-7.14 (m, 4H), 6.51 (d, J=5.4 Hz, 2H), 4.02 (s, 6H), 4.00 (s, 6H), 2.40 (s, 6H), 1.63-1.57 (m, 4H), 1.53-1.44 (m, 4H).

$^{13}$C NMR (101 MHz, 10% CD$_2$Cl$_2$ in CD$_3$OD) δ 173.9, 170.3, 162.3, 154.3, 151.4, 150.8, 149.2, 147.1, 136.6, 123.4, 122.2, 117.1, 107.3, 104.0, 100.4, 56.5, 56.4, 55.5, 45.7, 29.2, 17.9.

HRMS: (ESI TOF) m/z: [M+H]$^+$ Calcd for C$_{49}$H$_{47}$N$_6$O$_{10}$ m/z 879.3348; Found 879.3345.

IR: 3630, 3352, 2927, 2355, 1681, 1622, 1508, 1484, 1430, 1253, 1218, 850 cm$^{-1}$.

methyl 4-(1-((4-((6,7-dimethoxyquinolin-4-yl)oxy)phenyl)carbamoyl)cyclopropane-1-carboxamido)bicyclo[2.2.2]octane-1-carboxylate (15)

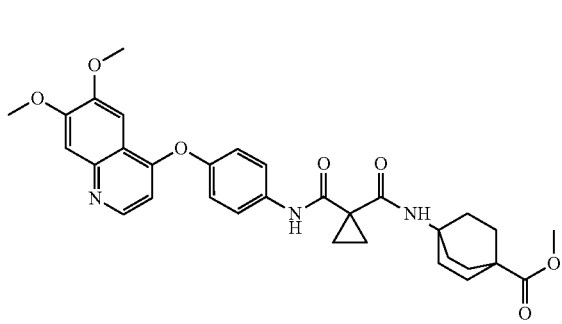

$^1$H NMR (400 MHz, CD$_3$OD) δ 8.41 (d, J=5.4 Hz, 1H), 7.69-7.63 (m, 2H), 7.62 (s, 1H), 7.36 (s, 1H), 7.25-7.17 (m, 2H), 6.53 (d, J=5.4 Hz, 1H), 4.02 (s, 3H), 4.00 (s, 3H), 3.63 (s, 3H), 2.02-1.83 (m, 12H), 1.53-1.40 (m, 4H).

$^{13}$C NMR (101 MHz, CD$_3$OD) δ 179.4, 171.9, 171.8, 162.7, 154.9, 152.0, 151.4, 149.6, 147.4, 137.0, 124.2, 122.5, 117.4, 107.5, 104.3, 100.6, 56.5 (2×OMe), 52.4, 52.3, 39.6, 31.0, 30.4, 29.6, 16.7.

HRMS: (ESI TOF) m/z: [M+H]$^+$ Calcd for C$_{32}$H$_{36}$N$_3$O$_7$ m/z 574.2548; Found 574.2548.

IR: 2940, 1728, 1665, 1623, 1507, 1480, 1432, 1349, 1251, 1216, 1169, 995, 852 cm$^{-1}$.

ethyl (2R,3R)-3-(1-((4-((6,7-dimethoxyquinolin-4-yl)oxy)phenyl)carbamoyl)cyclopropane-1-carboxamido)bicyclo[2.2.2]octane-2-carboxylate (16)

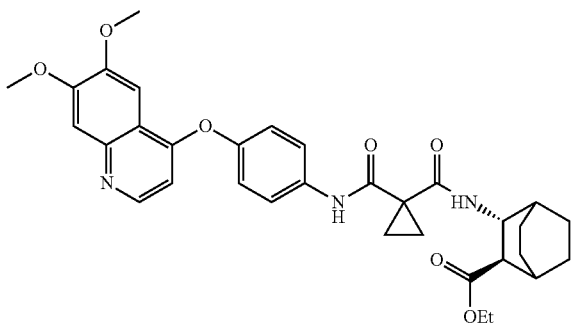 [SMILES: CCOC(=O)[C@@H]1C2CCC(CC2)[C@H]1NC(=O)C1(C(=O)Nc2ccc(Oc3ccnc4cc(OC)c(OC)cc34)cc2)CC1]

$^1$H NMR (400 MHz, CD$_3$OD) δ 8.41 (d, J=5.5 Hz, 1H), 7.74-7.65 (m, 2H), 7.63 (s, 1H), 7.36 (s, 1H), 7.26-7.17 (m, 2H), 6.53 (d, J=5.5 Hz, 1H), 4.40-4.33 (m, 1H), 4.15 (q, J=7.1 Hz, 2H), 4.02 (s, 3H), 4.00 (s, 3H), 2.59-2.50 (m, 1H), 1.97 (s, 1H), 1.78-1.65 (m, 4H), 1.64-1.41 (m, 9H), 1.25 (t, J=7.1 Hz, 3H).

$^{13}$C NMR (101 MHz, CD$_3$OD) δ 176.0, 172.6, 171.2, 162.8, 155.0, 151.9, 151.4, 149.6, 147.5, 137.2, 124.0, 122.6, 117.4, 107.5, 104.3, 100.6, 61.8, 56.5, 56.5, 51.6, 50.4, 30.6, 30.5, 29.7, 26.7, 25.1, 22.0, 20.4, 17.2, 17.0, 14.6.

HRMS: (ESI TOF) m/z: [M+H]$^+$ Calcd for C$_{33}$H$_{38}$N$_3$O$_7$ m/z 588.2705; Found 588.2705.

IR: 3633, 2940, 1727, 1665, 1507, 1480, 1218, 852, 772 cm$^{-1}$.

N-(3-azabicyclo[3.1.0]hexan-1-yl)-N-(4-((6,7-dimethoxyquinolin-4-yl)oxy)phenyl)cyclopropane-1,1-dicarboxamide (17)

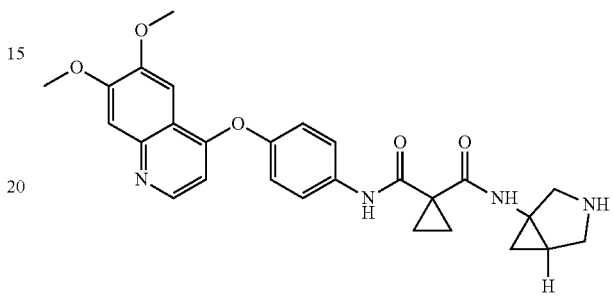

$^1$H NMR (400 MHz, CD$_3$OD) δ 8.41 (d, J=5.4 Hz, 1H), 7.75-7.67 (m, 2H), 7.63 (s, 1H), 7.36 (s, 1H), 7.25-7.17 (m, 2H), 6.53 (d, J=5.4 Hz, 1H), 4.02 (s, 3H), 4.00 (s, 3H), 3.23-3.10 (m, 2H), 2.98-2.86 (m, 2H), 1.68-1.60 (m, 1H), 1.60-1.53 (m, 2H), 1.50-1.41 (m, 2H), 1.01-0.89 (m, 2H).

$^{13}$C NMR (101 MHz, CD$_3$OD) δ 175.0, 170.5, 162.8, 154.9, 151.8, 151.4, 149.6, 147.4, 137.3, 123.7, 122.6, 117.4, 107.5, 104.3, 100.6, 56.5, 56.5, 51.0, 41.2, 30.1, 24.7, 17.6, 17.6, 14.4. 1 CH2NH of pyrrolidine moiety hidden under CD3O; verified by HMQC HRMS: (ESI TOF) m/z: [M+H]$^+$ Calcd for C$_{27}$H$_{29}$N$_4$O$_5$ m/z 489.2133; Found 489.2133.

IR: 3598, 3297, 2938, 1673, 1506, 1480, 1432, 1350, 1251, 1216, 825 cm$^{-1}$.

N-(3-acetyl-3-azabicyclo[3.1.0]hexan-1-yl)-N-(4-((6,7-dimethoxyquinolin-4-yl)oxy)phenyl)cyclopropane-1,1-dicarboxamide (18)

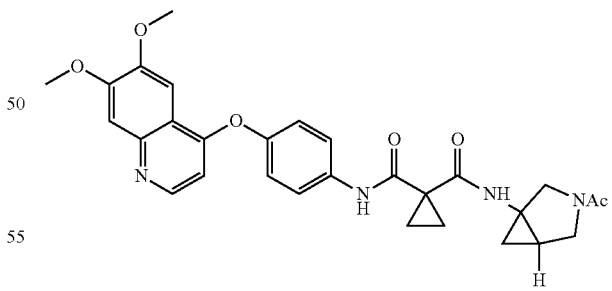

$^1$H NMR (400 MHz, CD$_3$OD) δ 8.41 (d, J=5.4 Hz, 1H), 7.77-7.65 (m, 2H), 7.63 (s, 1H), 7.36 (s, 1H), 7.26-7.14 (m, 2H), 6.53 (d, J=5.4 Hz, 1H), 4.02 (s, 3H), 4.00 (s, 3H), 3.95-3.84 (m, 1H), 3.71-3.54 (m, 2H), 3.46-3.39 (m, 1H), 2.01 (d, J=3.7 Hz, 3H), 1.86-1.72 (m, 1H), 1.64-1.52 (m, 2H), 1.52-1.39 (m, 2H), 1.20-1.09 (m, 1H), 0.79-0.69 (m, 1H).

$^{13}$C NMR (101 MHz, CD$_3$OD) δ 175.1, 175.0, 172.8, 172.7, 170.4, 162.8, 154.9, 151.8, 151.4, 149.6, 147.5, 137.3, 123.7, 122.6, 117.4, 107.5, 104.3, 100.6, 56.5, 56.5, 53.0, 51.1, 50.8, 39.8, 38.9, 30.2, 30.1, 24.3, 23.2, 22.2, 21.8, 17.8, 17.7, 17.7. 1 CH$_2$NH of pyrrolidine moiety hidden under CD$_3$OD; verified by HMQC.

HRMS: (ESI TOF) m/z: [M–H]$^+$ Calcd for C$_{29}$H$_{29}$N$_4$O$_6$ m/z 529.2092; Found 529.2087.

IR: 3291, 3061, 2933, 1678, 1625, 1507, 1480, 1432, 1350, 1251, 1218, 853 cm$^{-1}$.

N-(4-((6,7-dimethoxyquinolin-4-yl)oxy)phenyl)-1-((1R,3r,5S)-3-methoxy-8-azabicyclo[3.2.1]octane-8-carbonyl)cyclopropane-1-carboxamide (19)

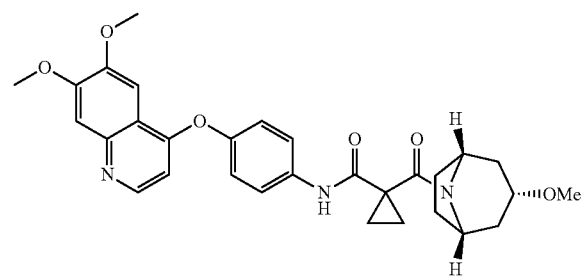 [SMILES: COc1cc2nccc(Oc3ccc(NC(=O)C4(C(=O)N5[C@@H]6CC[C@H]5C[C@@H](OC)C6)CC4)cc3)c2cc1OC]

$^1$H NMR (400 MHz, 10% CD$_2$Cl$_2$ in CD$_3$OD) δ 8.39 (d, J=5.4 Hz, 1H), 7.68-7.61 (m, 2H), 7.60 (s, 1H), 7.35 (s, 1H), 7.23-7.15 (m, 2H), 6.52 (d, J=5.4 Hz, 1H), 4.63-4.51 (m, 1H), 4.47-4.39 (m, 1H), 4.02 (s, 3H), 4.00 (s, 3H), 3.53-3.46 (m, 1H), 3.28 (s, 3H), 2.18-2.08 (m, 2H), 2.05-1.85 (m, 6H), 1.56-1.36 (m, 2H), 1.36-1.27 (m, 2H).

$^1$H NMR (400 MHz, 10% CD$_2$Cl$_2$ in CD$_3$OD) δ 8.39 (d, J=5.4 Hz, 1H), 7.68-7.61 (m, 2H), 7.60 (s, 1H), 7.35 (s, 1H), 7.23-7.15 (m, 2H), 6.52 (d, J=5.4 Hz, 1H), 4.58 (s, 1H), 4.40 (d, J=22.7 Hz, 1H), 4.02 (s, 3H), 4.00 (s, 3H), 3.50 (s, 1H), 3.28 (s, 3H), 2.12 (t, J=6.6 Hz, 2H), 2.05-1.85 (m, 6H), 1.46 (d, J=33.1 Hz, 2H), 1.31 (s, 2H).

HRMS: (ESI TOF) m/z: [M+H]$^+$ Calcd for C$_{30}$H$_{34}$N$_3$O$_6$ m/z 532.2442; Found 532.2436.

IR: 3629, 3245, 2941, 1614, 1505, 1480, 1218, 852, 772 cm$^{-1}$.

1-((1R,5S)-3-oxa-7-azabicyclo[3.3.1]nonane-7-carbonyl)-N-(4-((6,7-dimethoxyquinolin-4-yl)oxy)phenyl)cyclopropane-1-carboxamide (20)

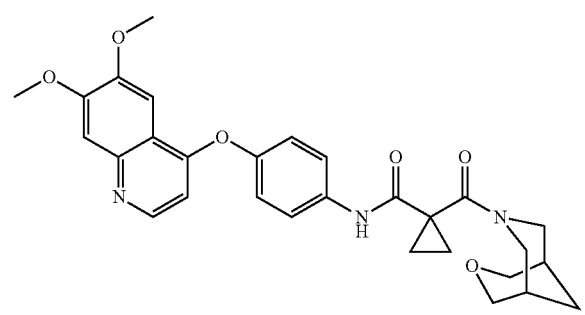 [SMILES: COc1cc2nccc(Oc3ccc(NC(=O)C4(C(=O)N5CC6COCC(C6)C5)CC4)cc3)c2cc1OC]

$^1$H NMR (400 MHz, CD$_3$OD) δ 8.44 (d, J=5.4 Hz, 1H), 7.84-7.71 (m, 2H), 7.65 (s, 1H), 7.38 (s, 1H), 7.28-7.16 (m, 2H), 6.55 (d, J=5.4 Hz, 1H), 4.45-4.35 (m, 1H), 4.21-4.10 (m, 1H), 4.04 (s, 3H), 4.03 (s, 3H), 3.96 (d, J=11.5 Hz, 1H), 3.88 (d, J=11.5 Hz, 1H), 3.77 (d, J=11.5 Hz, 1H), 3.60 (d, J=13.2 Hz, 1H), 3.10 (d, J=13.2 Hz, 1H), 2.16-2.07 (m, 1H), 2.07-1.93 (m, 1H), 1.93-1.83 (m, 2H), 1.68-1.51 (m, 2H), 1.44-1.32 (m, 1H), 1.34-1.25 (m, 1H). 1 proton is hidden inside CD$_3$OD.

$^{13}$C NMR (101 MHz, CD$_3$OD) δ 170.6, 169.8, 162.7, 154.9, 152.0, 151.4, 149.6, 147.4, 137.2, 123.9, 122.4, 117.4, 107.5, 104.3, 100.6, 73.5, 72.8, 56.5, 56.5, 52.1, 32.0, 31.9, 31.2, 30.8, 16.7.

HRMS: (ESI TOF) m/z: [M+H]$^+$ Calcd for C$_{29}$H$_{32}$N$_3$O$_6$ m/z 518.2286; Found 518.2280.

IR: 3261, 3059, 2939, 2846, 1670, 1623, 1552, 1507, 1478, 1432, 1250, 1214, 1170, 996, 855, 772 cm$^{-1}$.

EXO-1-(3-cyano-8-azabicyclo[3.2.1]octane-8-carbonyl)-N-(4-((6,7-dimethoxyquinolin-4-yl)oxy)phenyl)cyclopropane-1-carboxamide (21)

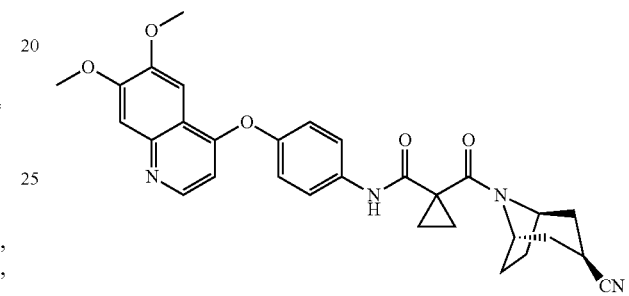

$^1$H NMR (400 MHz, CD$_3$OD) δ 8.38 (d, J=5.4 Hz, 1H), 7.69-7.61 (m, 2H), 7.60 (s, 1H), 7.34 (s, 1H), 7.24-7.12 (m, 2H), 6.51 (d, J=5.4 Hz, 1H), 4.02 (s, 3H), 4.00 (s, 3H), 3.24-2.09 (m, 1H), 2.11-1.87 (m, 6H), 1.87-1.71 (m, 2H), 1.55-1.42 (m, 2H), 1.39-1.28 (m, 2H). 2× amide-NCH proton did not appear. Refer to spectrum in DMSO-d$_6$.

$^1$H NMR (400 MHz, DMSO-d$_6$) δ 9.93 (s, 1H), 8.46 (d, J=5.2 Hz, 1H), 7.84-7.69 (m, 2H), 7.50 (s, 1H), 7.39 (s, 1H), 7.29-7.11 (m, 2H), 6.44 (d, J=5.2 Hz, 1H), 4.55 (s, 1H), 4.26 (s, 1H), 3.94 (s, 3H), 3.92 (s, 3H), 2.02-1.57 (m, 8H), 1.42-1.16 (m, 4H). CHCN proton is hidden inside the water peak of DMSO-d$_6$; refer to spectrum done in CD$_3$OD.

$^{13}$C NMR (101 MHz, DMSO-d$_6$) δ 168.2, 163.8, 159.8, 152.5, 149.6, 149.3, 148.8, 146.4, 136.3, 122.3, 122.0, 121.1, 115.1, 107.8, 103.1, 99.1, 55.7, 55.7, 53.6, 50.7, 33.8, 33.2, 31.0, 27.3, 25.8, 19.9, 13.2.

HRMS: (ESI TOF) m/z: [M+H]$^+$ Calcd for C$_{30}$H$_{31}$N$_4$O$_5$ m/z 527.2289; Found 527.2283.

IR: 3252, 2964, 1677, 1623, 1506, 1481, 1350, 1249, 1217, 998, 853, 772 cm$^{-1}$.

EXO-3-(1-((4-((6,7-dimethoxyquinolin-4-yl)oxy)phenyl)carbamoyl)cyclopropane-1-carbonyl)-3-azabicyclo[3.1.0]hexane-6-carboxamide (22)

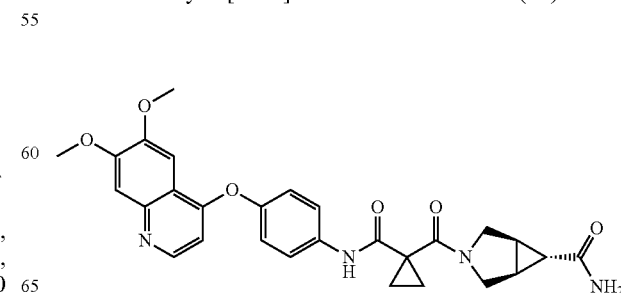

¹H NMR (400 MHz, CD₃OD) δ 8.44 (d, J=5.4 Hz, 1H), 7.71-7.66 (m, 2H), 7.65 (s, 1H), 7.39 (s, 1H), 7.32-7.20 (m, 2H), 6.56 (d, J=5.4 Hz, 1H), 4.04 (s, 3H), 4.03 (s, 3H), 4.02-3.91 (m, 2H), 3.81-3.71 (m, 1H), 3.63-3.53 (m, 1H), 2.21-2.03 (m, 2H), 1.78-1.63 (m, 1H), 1.63-1.50 (m, 1H), 1.50-1.38 (m, 2H), 1.29-1.17 (m, 1H).

¹H NMR (400 MHz, DMSO-d₆) δ 9.76 (s, 1H), 8.47 (d, J=5.2 Hz, 1H), 7.82-7.63 (m, 2H), 7.50 (s, 1H), 7.45 (s, 1H), 7.39 (s, 1H), 7.28-7.16 (m, 2H), 6.85 (s, 1H), 6.45 (d, J=5.2 Hz, 1H), 3.94 (s, 3H), 3.93 (s, 3H), 3.88-3.78 (m, 1H), 3.78-3.67 (m, 1H), 3.62-3.50 (m, 1H), 3.47-3.37 (m, 2H), 2.00-1.88 (m, 1H), 1.88-1.79 (m, 1H), 1.62-1.49 (m, 1H), 1.46-1.37 (m, 1H), 1.34-1.18 (m, 2H), 1.06-0.92 (m, 1H).

¹³C NMR (101 MHz, DMSO-d₆) δ 172.3, 168.0, 167.0, 159.9, 152.5, 149.7, 149.3, 148.8, 146.4, 136.2, 122.6, 121.1, 115.1, 107.9, 103.2, 99.1, 55.7, 55.7, 48.0, 47.7, 32.0, 24.4, 24.0, 22.8, 14.1, 13.6.

HRMS: (ESI TOF) m/z: [M+H]⁺ Calcd for $C_{28}H_{29}N_4O_6$ m/z 517.2082 Found 517.2075.

IR: 3459, 3240, 2951, 1682, 1621, 1506, 1479, 1432, 1218, 850, 772 cm⁻¹.

ENDO-N-(4-((6,7-dimethoxyquinolin-4-yl)oxy)phenyl)-N-((1R,3r,5S)-8-methyl-8-azabicyclo[3.2.1]octan-3-yl)cyclopropane-1,1-dicarboxamide (23)

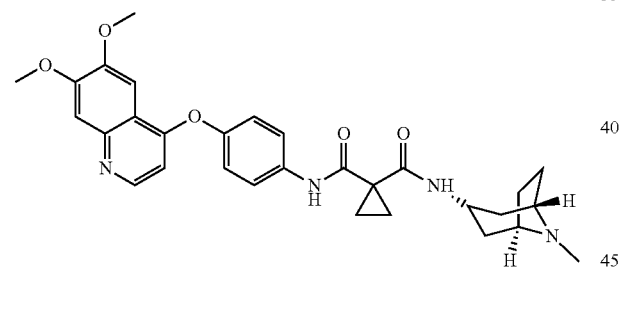

¹H NMR (400 MHz, CD₃OD) δ 8.44 (d, J=5.4 Hz, 1H), 7.74-7.67 (m, 2H), 7.65 (s, 1H), 7.39 (s, 1H), 7.29-7.21 (m, 2H), 6.57 (d, J=5.4 Hz, 1H), 4.05 (s, 3H), 4.04-3.99 (m, 3+1H), 3.29-3.17 (m, 2H), 2.35 (s, 3H), 2.26-2.13 (m, 4H), 2.06-1.94 (m, 2H), 1.84-1.78 (m, 1H), 1.78-1.75 (m, 1H), 1.59 (s, 4H).

¹³C NMR (101 MHz, CD₃OD) δ 172.7, 171.0, 162.7, 154.9, 152.3, 151.4, 149.6, 147.5, 136.8, 124.8, 122.5, 117.4, 107.5, 104.3, 100.6, 61.4, 56.5, 56.5, 48.4, 42.4, 40.2, 36.4, 30.0, 25.9, 17.0.

HRMS: (ESI TOF) m/z: [M+H]⁺ Calcd for $C_{30}H_{35}N_4O_5$ m/z 531.2602; Found 531.2602.

IR: 3295, 2942, 1668, 1506, 1480, 1432, 1349, 1251, 1215, 994, 850 cm⁻¹.

N-(bicyclo[2.2.2]octan-1-yl)-N-(4-((6,7-dimethoxyquinolin-4-yl)oxy)phenyl)cyclopropane-1,1-dicarboxamide (24)

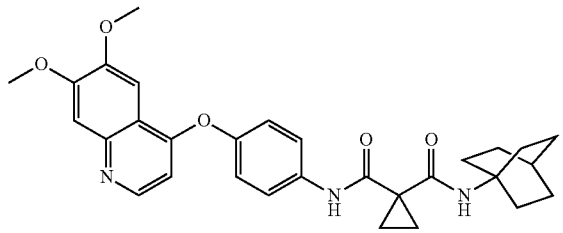 [SMILES: COc1cc2nccc(Oc3ccc(NC(=O)C4(C(=O)NC56CCC(CC5)CC6)CC4)cc3)c2cc1OC]

¹H NMR (400 MHz, 10% CD₂Cl₂ in CD₃OD) δ 8.40 (d, J=5.4 Hz, 1H), 7.70-7.62 (m, 2H), 7.61 (s, 1H), 7.35 (s, 1H), 7.26-7.15 (m, 2H), 6.52 (d, J=5.4 Hz, 1H), 4.02 (s, 3H), 4.00 (s, 3H), 1.94-1.82 (m, 6H), 1.74-1.61 (m, 6H), 1.60-1.52 (m, 1H), 1.52-1.38 (m, 4H).

¹H NMR (400 MHz, CD₂Cl₂) δ 10.71 (s, 1H), 8.44 (d, J=5.3 Hz, 1H), 7.75-7.61 (m, 2H), 7.56 (s, 1H), 7.38 (s, 1H), 7.22-7.10 (m, 2H), 6.45 (d, J=5.3 Hz, 1H), 4.00 (s, 3H), 3.99 (s, 3H), 2.01-1.57 (m, 15H), 1.26-1.15 (m, 2H).

¹³C NMR (101 MHz, CD₂Cl₂) δ 171.7, 168.4, 161.1, 153.4, 150.8, 150.1, 149.1, 147.4, 136.3, 122.1, 121.8, 116.4, 108.3, 103.7, 100.0, 56.4, 56.4, 52.0, 30.6, 29.4, 26.5, 24.4, 17.2.

HRMS: (ESI TOF) m/z: [M+H]⁺ Calcd for $C_{30}H_{34}N_3O_5$ m/z 516.2493; Found 516.2493.

IR: 3635, 1682, 1480, 1214, 854 cm⁻¹.

N-((1s,4s)-bicyclo[2.2.1]heptan-1-yl)-N-(4-((6,7-dimethoxyquinolin-4-yl)oxy)phenyl)cyclopropane-1,1-dicarboxamide (25)

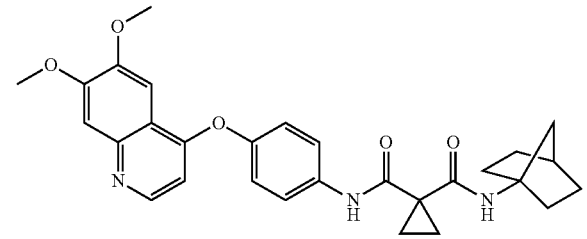 [SMILES: COc1cc2nccc(Oc3ccc(NC(=O)C4(C(=O)NC56CCC(CC5)C6)CC4)cc3)c2cc1OC]

¹H NMR (400 MHz, CD₃OD) δ 8.40 (d, J=5.4 Hz, 1H), 7.72-7.63 (m, 2H), 7.61 (s, 1H), 7.34 (s, 1H), 7.25-7.14 (m, 2H), 6.52 (d, J=5.4 Hz, 1H), 4.01 (s, 3H), 3.99 (s, 3H), 2.16 (s, 1H), 1.83-1.72 (m, 5H), 1.75-1.67 (m, 2H), 1.59-1.33 (m, 7H).

¹³C NMR (101 MHz, CD₃OD) δ 172.9, 171.4, 162.7, 155.0, 151.9, 151.4, 149.6, 147.4, 137.1, 123.9, 122.5, 117.4, 107.5, 104.3, 100.6, 64.0, 56.5, 56.5, 42.6, 36.4, 34.3, 30.9, 30.6, 17.0.

HRMS: (ESI TOF) m/z: [M+H]⁺ Calcd for $C_{29}H_{32}N_3O_5$ m/z 502.2337; Found 502.2334.

IR: 3386, 1682, 1530, 260+, 1480, 1215, 850 cm⁻¹.

1-((1s,5s)-9-azabicyclo[3.3.1]nonane-9-carbonyl)-N-(4-((6,7-dimethoxyquinolin-4-yl)oxy)phenyl)cyclopropane-1-carboxamide (26)

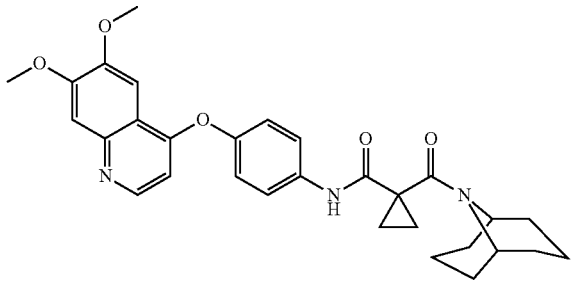 [SMILES: COc1cc2nccc(Oc3ccc(NC(=O)C4(C(=O)N5C6CCCC5CCC6)CC4)cc3)c2cc1OC]

$^1$H NMR (400 MHz, 10% CD$_2$Cl$_2$ in CD$_3$OD) δ 8.39 (d, J=5.4 Hz, 1H), 7.69-7.62 (m, 2H), 7.60 (s, 1H), 7.35 (s, 1H), 7.23-7.14 (m, 2H), 6.52 (d, J=5.4 Hz, 1H), 4.71-4.61 (m, 1H), 4.44-4.32 (m, 1H), 4.02 (s, 3H), 4.00 (s, 3H), 2.24-2.03 (m, 2H), 1.97-1.81 (m, 4H), 1.80-1.71 (m, 4H), 1.67-1.55 (m, 2H), 1.52-1.43 (m, 2H), 1.37-1.28 (m, 2H).

$^{13}$C NMR (101 MHz, 10% CD$_2$Cl$_2$ in CD$_3$OD) δ 170.0, 168.0, 162.3, 154.5, 151.7, 151.0, 149.3, 147.2, 136.7, 123.7, 122.3, 117.2, 107.4, 104.2, 100.5, 56.5, 56.5, 50.8, 46.2, 32.1, 30.8, 30.0, 20.7, 14.1.

HRMS: (ESI TOF) m/z: [M+H]$^+$ Calcd for C$_{30}$H$_{34}$N$_3$O$_5$ m/z 516.2493; Found 516.2489.

IR: 2940, 1676, 1606, 1507, 1481, 1350, 1250, 1216, 997, 855 cm$^{-1}$.

1-(3-azabicyclo[3.1.0]hexane-3-carbonyl)-N-(4-((6,7-dimethoxyquinolin-4-yl)oxy)phenyl)cyclopropane-1-carboxamide (27)

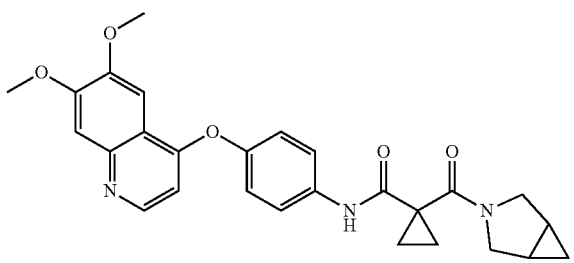 [SMILES: COc1cc2nccc(Oc3ccc(NC(=O)C4(C(=O)N5CC6CC6C5)CC4)cc3)c2cc1OC]

$^1$H NMR (400 MHz, 10% CD$_2$Cl$_2$ in CD$_3$OD) δ 8.40 (d, J=5.4 Hz, 1H), 7.68-7.61 (m, 2H), 7.60 (s, 1H), 7.34 (s, 1H), 7.25-7.17 (m, 2H), 6.52 (d, J=5.4 Hz, 1H), 4.01 (s, 3H), 3.99 (s, 3H), 3.92-3.76 (m, 2H), 3.69-3.60 (m, 1H), 3.49-3.39 (m, 1H), 1.70-1.55 (m, 2H), 1.56-1.48 (m, 1H), 1.47-1.36 (m, 2H), 1.25-1.13 (m, 1H), 0.79-0.69 (m, 1H), 0.18-0.11 (m, 1H).

$^{13}$C NMR (101 MHz, 10% CD$_2$Cl$_2$ in CD$_3$OD) δ 169.9, 168.5, 161.7, 153.8, 151.1, 150.3, 148.8, 146.7, 136.1, 122.9, 121.9, 116.6, 107.2, 103.7, 100.1, 56.4, 56.3, 32.9, 16.1, 14.8, 14.3, 9.4.

HRMS: (ESI TOF) m/z: [M+H]$^+$ Calcd for C$_{27}$H$_{28}$N$_3$O$_5$ m/z 474.2024; Found 474.2021.

IR: 3252, 1675, 1617, 1508, 1481, 1433, 1350, 1252, 1216, 1168, 996, 853 cm$^{-1}$.

N-((3R,5R)-adamantan-1-yl)-N-(4-((6,7-dimethoxyquinolin-4-yl)oxy)phenyl)cyclopropane-1,1-dicarboxamide (28)

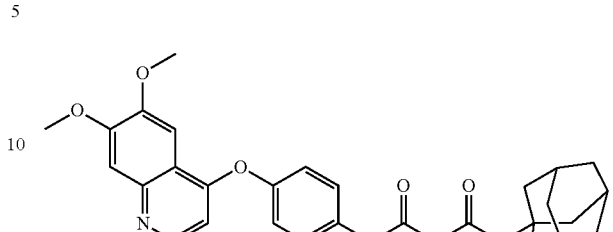

$^1$H NMR (400 MHz, 10% CD$_2$Cl$_2$ in CD$_3$OD) δ 8.39 (d, J=5.4 Hz, 1H), 7.69-7.62 (m, 2H), 7.61 (s, 1H), 7.34 (s, 1H), 7.24-7.15 (m, 2H), 6.51 (d, J=5.4 Hz, 1H), 4.02 (s, 3H), 4.00 (s, 3H), 2.11-2.00 (m, 9H), 1.76-1.69 (m, 6H), 1.52-1.46 (m, 2H), 1.46-1.41 (m, 2H).

$^{13}$C NMR (101 MHz, 10% CD$_2$Cl$_2$ in CD$_3$OD) δ 171.5, 171.1, 162.4, 154.5, 151.7, 151.0, 149.3, 147.2, 136.6, 123.9, 122.3, 117.2, 107.4, 104.2, 100.5, 56.5, 56.5, 53.2, 42.1, 37.2, 30.8, 30.6, 16.6.

HRMS: (ESI TOF) m/z: [M+H]$^+$ Calcd for C$_{32}$H$_{36}$N$_3$O$_5$ m/z 542.265; Found 542.2650.

IR: 3294, 2904, 1651, 1528, 1508, 1482, 1432, 1350, 1219, 851 cm$^{-1}$.

3-(1-((4-((6,7-dimethoxyquinolin-4-yl)oxy)phenyl)carbamoyl)cyclopropane-1-carboxamido)bicyclo[1.1.1]pentane-1-carboxylic Acid Hydrochloride (29)

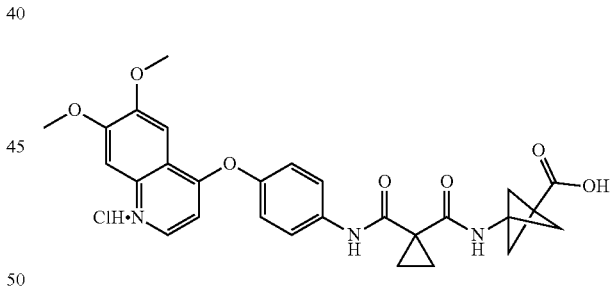

$^1$H NMR (400 MHz, CD$_3$OD) δ 8.41 (d, J=5.4 Hz, 1H), 7.75-7.65 (m, 2H), 7.63 (s, 1H), 7.35 (s, 1H), 7.26-7.15 (m, 2H), 6.53 (d, J=5.4 Hz, 1H), 4.01 (s, 3H), 4.00 (s, 3H), 2.24 (s, 6H), 1.59-1.46 (m, 2H), 1.46-1.38 (m, 2H).

$^{13}$C NMR (101 MHz, CD$_3$OD) δ 178.8, 174.3, 170.8, 162.8, 161.4, 154.9, 151.6, 151.3, 149.6, 147.4, 123.9, 122.5, 117.4, 107.5, 104.3, 100.7, 56.5, 56.5, 55.0, 46.3, 39.6, 30.1, 17.5.

HRMS: (ESI TOF) m/z: [M−HCl+H]$^+$ Calcd for C$_{28}$H$_{28}$N$_3$O$_7$ m/z 518.1922; Found 518.1919; [M−HCl−H]$^+$ Calcd for C$_{28}$H$_{26}$N$_3$O$_7$ m/z 516.1776; Found 516.1776.

IR: 3279, 2923, 1598, 1505, 1279, 1224, 1195, 891, 837 cm$^{-1}$.

N-(4-((6,7-dimethoxyquinolin-4-yl)oxy)phenyl)-N-(3-(methoxymethyl)bicyclo[1.1.1]pentan-1-yl)cyclopropane-1,1-dicarboxamide (30)

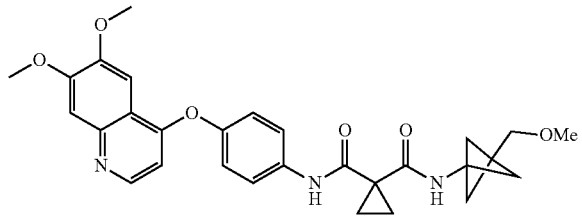 [SMILES: COCC12CC(NC(=O)C3(C(=O)Nc4ccc(Oc5ccnc6cc(OC)c(OC)cc56)cc4)CC3)(C1)C2]

$^1$H NMR (400 MHz, 10% CD$_2$Cl$_2$ in CD$_3$OD) δ 8.39 (d, J=5.4 Hz, 1H), 7.74-7.65 (m, 2H), 7.61 (s, 1H), 7.35 (s, 1H), 7.25-7.13 (m, 2H), 6.51 (d, J=5.4 Hz, 1H), 4.02 (s, 3H), 4.00 (s, 3H), 3.48 (s, 2H), 3.35 (s, 3H), 2.03 (s, 6H), 1.61-1.53 (m, 2H), 1.50-1.41 (m, 2H).

$^{13}$C NMR (101 MHz, 10% CD$_2$Cl$_2$ in CD$_3$OD) δ 174.0, 170.6, 162.6, 154.7, 151.6, 151.1, 149.4, 147.3, 137.0, 123.5, 122.4, 117.3, 107.4, 104.2, 100.5, 72.5, 59.3, 56.5, 56.5, 53.0, 47.2, 37.3, 29.6, 17.7.

HRMS: (ESI TOF) m/z: [M+H]$^+$ Calcd for C$_{29}$H$_{32}$N$_3$O$_6$ m/z 518.2286; Found 518.2284.

IR: 3254, 2976, 2832, 1671, 1506, 1482, 1434, 1346, 1251, 1213, 855 cm$^{-1}$.

methyl 3-(1-((4-((6,7-dimethoxyquinolin-4-yl)oxy)phenyl)carbamoyl)cyclopropane-1-carboxamido)bicyclo[1.1.1]pentane-1-carboxylate (31)

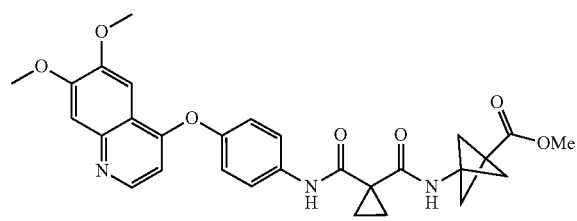 [SMILES: COC(=O)C12CC(NC(=O)C3(C(=O)Nc4ccc(Oc5ccnc6cc(OC)c(OC)cc56)cc4)CC3)(C1)C2]

$^1$H NMR (400 MHz, 10% CD$_2$Cl$_2$ in CD$_3$OD) δ 8.40 (d, J=5.4 Hz, 1H), 7.72-7.66 (m, 2H), 7.62 (s, 1H), 7.35 (s, 1H), 7.23-7.16 (m, 2H), 6.51 (d, J=5.4 Hz, 1H), 4.02 (s, 3H), 4.00 (s, 3H), 3.68 (s, 3H), 2.35 (s, 6H), 1.61-1.54 (m, 2H), 1.50-1.42 (m, 2H).

$^{13}$C NMR (101 MHz, 10% CD$_2$Cl$_2$ in CD$_3$OD) δ 174.3, 171.6, 170.5, 162.6, 154.7, 151.7, 151.2, 149.4, 147.3, 137.0, 123.6, 122.4, 117.3, 107.4, 104.2, 100.6, 56.5, 56.5, 55.1, 52.3, 46.7, 37.0, 29.7, 17.8.

HRMS: (ESI TOF) m/z: [M+H]$^+$ Calcd for C$_{29}$H$_{30}$N$_3$O$_7$ m/z 532.2079; Found 532.2076.

IR: 3601, 2965, 1662, 1508, 1481, 1431, 1348, 1217, 850, 772 cm$^{-1}$.

N-(4-((6,7-dimethoxyquinolin-4-yl)oxy)phenyl)-N-(3-(hydroxymethyl)bicyclo[1.1.1]pentan-1-yl)cyclopropane-1,1-dicarboxamide (32)

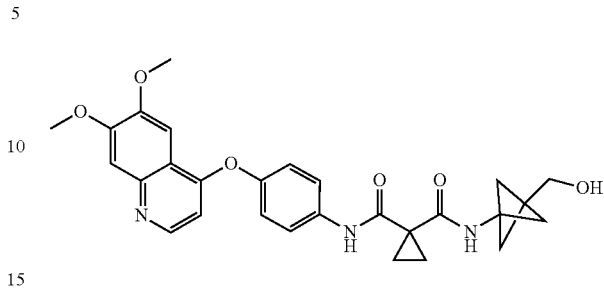

$^1$H NMR (400 MHz, 10% CD$_2$Cl$_2$ in CD$_3$OD) δ 8.39 (d, J=5.4 Hz, 1H), 7.73-7.66 (m, 2H), 7.61 (s, 1H), 7.34 (s, 1H), 7.24-7.16 (m, 2H), 6.51 (d, J=5.4 Hz, 1H), 4.02 (s, 3H), 4.00 (s, 3H), 3.62 (s, 2H), 2.01 (s, 6H), 1.62-1.53 (m, 2H), 1.50-1.41 (m, 2H).

$^{13}$C NMR (101 MHz, 10% CD$_2$Cl$_2$ in CD$_3$OD) δ 173.9, 170.6, 162.5, 154.6, 151.6, 151.1, 149.3, 147.2, 136.9, 123.5, 122.4, 117.2, 107.4, 104.1, 100.5, 62.0, 56.5, 56.5, 52.2, 47.1, 38.8, 29.6, 17.7.

HRMS: (ESI TOF) m/z: [M+H]$^+$ Calcd for C$_{28}$H$_{30}$N$_3$O$_6$ m/z 504.2129; Found 504.2126.

IR: 3227, 2978 1676, 1527, 1507, 1485, 1351, 1235, 1221 844, 772 cm$^{-1}$.

N-(3-cyanobicyclo[1.1.1]pentan-1-yl)-N-(4-((6,7-dimethoxyquinolin-4-yl)oxy)phenyl)cyclopropane-1,1-dicarboxamide (33)

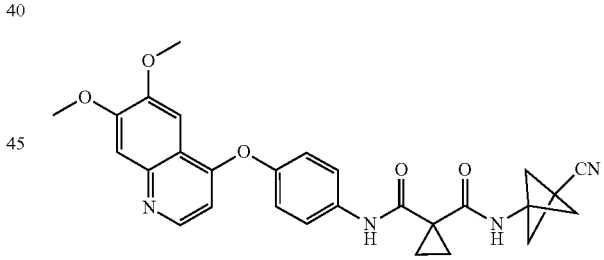

$^1$H NMR (400 MHz, 10% CD$_2$Cl$_2$ in CD$_3$OD) δ 8.39 (d, J=5.4 Hz, 1H), 7.70-7.63 (m, 2H), 7.61 (s, 1H), 7.34 (s, 1H), 7.22-7.15 (m, 2H), 6.50 (d, J=5.4 Hz, 1H), 4.02 (s, 3H), 4.00 (s, 3H), 2.56 (s, 6H), 1.65-1.57 (m, 2H), 1.49-1.42 (m, 2H).

$^{13}$C NMR (101 MHz, 10% CD$_2$Cl$_2$ in CD$_3$OD) δ 174.4, 170.1, 162.4, 154.5, 151.5, 150.9, 149.2, 147.1, 136.7, 123.4, 122.3, 118.0, 117.1, 107.4, 104.1, 100.5, 57.5, 56.5, 56.5, 29.2, 22.7, 18.1. One of the BCP tertiary carbon hidden inside CD$_3$OD solvent peak.

HRMS: (ESI TOF) m/z: [M+H]$^+$ Calcd for C$_{28}$H$_{27}$N$_4$O$_5$ m/z 499.1976; Found 499.1976.

IR: 2995, 2390, 1662, 1508, 1480, 1434, 1347, 1253, 1219, 993, 850 cm$^{-1}$.

N1-((1s,4s)-bicyclo[2.2.1]heptan-1-yl)-N3-(4-((6,7-dimethoxyquinolin-4 yl)oxy)phenyl)bicyclo[1.1.1]pentane-1,3-dicarboxamide (34)

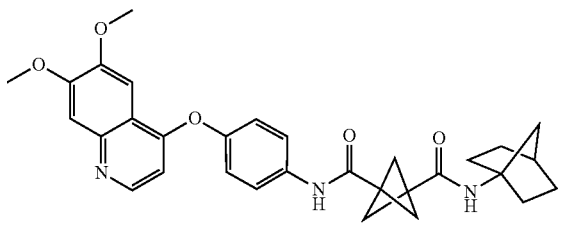 [SMILES: COc1cc2nccc(Oc3ccc(NC(=O)C45CC(C(=O)NC67CCC(CC6)C7)(C4)C5)cc3)c2cc1OC]

$^1$H NMR (400 MHz, 10% CD$_2$Cl$_2$ in CD$_3$OD) δ 8.39 (d, J=5.4 Hz, 1H), 7.78-7.70 (m, 2H), 7.61 (s, 1H), 7.35 (s, 1H), 7.23-7.15 (m, 2H), 6.52 (d, J=5.4 Hz, 1H), 4.02 (s, 3H), 4.00 (s, 3H), 2.34 (s, 6H), 2.20-2.08 (m, 1H), 1.89-1.71 (m, 6H), 1.71-1.59 (m, 2H), 1.43-1.35 (m, 2H).

$^{13}$C NMR (101 MHz, 10% CD$_2$Cl$_2$ in CD$_3$OD) δ 172.1, 170.6, 162.5, 154.6, 151.7, 151.1, 149.3, 147.2, 136.9, 123.6, 122.3, 117.2, 107.4, 104.2, 100.5, 63.5, 56.5, 56.5, 52.8, 42.4, 39.7, 39.6, 36.2, 34.2, 30.7.

HRMS: (ESI TOF) m/z: [M+H]$^+$ Calcd for C$_{31}$H$_{34}$N$_3$O$_5$ m/z 528.2493; Found 528.2491.

IR: 3298, 2883, 1643, 1535, 1506, 1481, 1248, 1218, 855 cm$^{-1}$.

3-(3-azabicyclo[3.1.0]hexane-3-carbonyl)-N-(4-((6,7-dimethoxyquinolin-4-yl)oxy)phenyl)bicyclo[1.1.1]pentane-1-carboxamide (35)

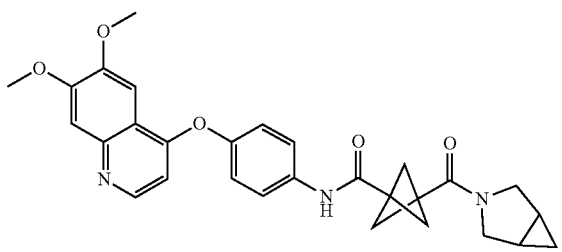 [SMILES: COc1cc2nccc(Oc3ccc(NC(=O)C45CC(C(=O)N6CC7CC7C6)(C4)C5)cc3)c2cc1OC]

$^1$H NMR (400 MHz, 20% CD$_2$Cl$_2$ in CD$_3$OD) δ 8.38 (d, J=5.4 Hz, 1H), 7.77-7.69 (m, 2H), 7.59 (s, 1H), 7.33 (s, 1H), 7.22-7.12 (m, 2H), 6.49 (d, J=5.4 Hz, 1H), 4.38 (s, 1H), 4.03 (s, 3H), 4.02 (s, 3H), 3.81 (d, J=10.2 Hz, 1H), 3.73 (d, J=12.1 Hz, 1H), 3.68 (dd, J=10.2, 4.5 Hz, 1H), 3.43 (dd, J=12.1, 4.5 Hz, 1H), 2.43 (qd, J=9.5, 1.8 Hz, 6H), 1.74-1.63 (m, 1H), 1.62-1.51 (m, 1H), 0.8-0.72 (m, 1H), 0.18-0.07 (m, 1H).

$^{13}$C NMR (101 MHz, 20% CD$_2$Cl$_2$ in CD$_3$OD) δ 170.2, 169.9, 162.2, 154.2, 151.4, 150.6, 149.1, 147.0, 136.5, 123.3, 122.1, 117.0, 107.3, 104.0, 100.4, 56.5, 56.5, 53.4, 50.1, 49.9, 41.2, 39.6, 17.2, 14.8, 10.4.

HRMS: (ESI TOF) m/z: [M+H]$^+$ Calcd for C$_{29}$H$_{30}$N$_3$O$_5$ m/z 500.218; Found 500.2177.

IR: 3321, 2876, 1683, 1615, 1512, 1478, 1218, 885 cm$^{-1}$.

N1-cyclopropyl-N3-(4-((6,7-dimethoxyquinolin-4-yl)oxy)phenyl)bicyclo[1.1.1]pentane-1,3-dicarboxamide (36)

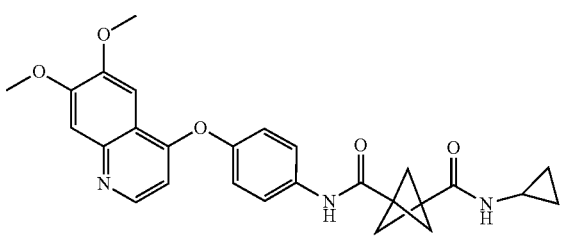 [SMILES: COc1cc2nccc(Oc3ccc(NC(=O)C45CC(C(=O)NC6CC6)(C4)C5)cc3)c2cc1OC]

$^1$H NMR (400 MHz, 10% CD$_2$Cl$_2$ in CD$_3$OD) δ 8.39 (d, J=5.4 Hz, 1H), 7.77-7.67 (m, 2H), 7.61 (s, 1H), 7.34 (s, 1H), 7.23-7.13 (m, 2H), 6.51 (d, J=5.4 Hz, 1H), 4.02 (s, 3H), 4.00 (s, 3H), 2.72-2.59 (m, 1H), 2.32 (s, 6H), 0.79-0.66 (dt, J=7.1, 3.4 Hz, 2H), 0.60-0.48 (m, 2H).

$^{13}$C NMR (101 MHz, 10% CD$_2$Cl$_2$ in CD$_3$OD) δ 173.4, 170.3, 162.4, 154.5, 151.6, 150.9, 149.2, 147.1, 136.7, 123.5, 122.2, 117.1, 107.3, 104.1, 100.5, 56.5, 56.5, 52.7, 39.8, 39.0, 23.1, 6.2.

HRMS: (ESI TOF) m/z: [M+H]$^+$ Calcd for C$_{27}$H$_{28}$N$_3$O$_5$ m/z 474.2024; Found 474.2025.

IR: 3307, 2918, 1650, 1528, 1509, 1482, 1251, 1218, 1033, 847 cm$^{-1}$.

Example 1: GI$_{50}$ in HCCLM3 Cells

To investigate the effects of compounds on hepatocellular carcinoma (HCC) cell viability, HCCLM3 cells (HCC cells with high metastatic potential) were incubated with increasing concentrations of test compounds for 72 hours. Cell viability was evaluated at the end of incubation period by MTS assay. The concentration that inhibited cell growth by 50% over the control was determined as GI$_{50}$. All samples were evaluated in triplicates.

As set forth in Table 1 below, GI$_{50}$ values are defined as follows: GI$_{50}$≤10 μM (+++); GI$_{50}$>10 μM and ≤20 μM (++); GI$_{50}$>20 μM (+).

TABLE 1

Growth inhibition (GI$_{50}$) values for Representative Compounds against HCCLM3 cell lines.

| IUPAC name | Compound number | HCCLM3 activity range |
|---|---|---|
| N-(bicyclo[1.1.1]pentan-1-yl)-N-(4-((6,7-dimethoxyquinolin-4-yl)oxy)phenyl)cyclopropane-1,1-dicarboxamide | 1 | +++ |
| N-(4-((6,7-dimethoxyquinolin-4-yl)oxy)phenyl)-N-(3-phenylbicyclo[1.1.1]pentan-1-yl)cyclopropane-1,1-dicarboxamide | 2 | + |

TABLE 1-continued

Growth inhibition ($GI_{50}$) values for Representative Compounds against HCCLM3 cell lines.

| IUPAC name | Compound number | HCCLM3 activity range |
|---|---|---|
| $N^1$-(4-((6,7-dimethoxyquinolin-4-yl)oxy)phenyl)-$N^3$-(3-fluorobicyclo[1.1.1]pentan-1-yl)bicyclo[1.1.1]pentane-1,3-dicarboxamide | 3 | + |
| N-(4-((6,7-dimethoxyquinolin-4-yl)oxy)phenyl)-N-(3-fluorobicyclo[1.1.1]pentan-1-yl)cyclopropane-1,1-dicarboxamide | 4 | +++ |
| 3-(1-((4-((6,7-dimethoxyquinolin-4-yl)oxy)phenyl)carbamoyl)cyclopropane-1-carboxamido)bicyclo[1.1.1]pentan-1-yl benzoate | 5 | + |
| N-(4-((6,7-dimethoxyquinolin-4-yl)oxy)phenyl)-N-(3-hydroxybicyclo[1.1.1]pentan-1-yl)cyclopropane-1,1-dicarboxamide | 6 | + |
| N-(3-carbamoylbicyclo[1.1.1]pentan-1-yl)-N-(4-((6,7-dimethoxyquinolin-4-yl)oxy)phenyl)cyclopropane-1,1-dicarboxamide | 7 | + |
| N-(4-((6,7-dimethoxyquinolin-4-yl)oxy)phenyl)-N-(3-(dimethylcarbamoyl)bicyclo[1.1.1]pentan-1-yl)cyclopropane-1,1-dicarboxamide | 8 | + |
| N-(4-((6,7-dimethoxyquinolin-4-yl)oxy)phenyl)-N-(3-(pyrazin-2-yl)bicyclo[1.1.1]pentan-1-yl)cyclopropane-1,1-dicarboxamide | 9 | + |
| N-(4-((6,7-dimethoxyquinolin-4-yl)oxy)phenyl)-N-(3-methylbicyclo[1.1.1]pentan-1-yl)cyclopropane-1,1-dicarboxamide | 10 | +++ |
| N-(4-((6,7-dimethoxyquinolin-4-yl)oxy)phenyl)-N-(3-(trifluoromethyl)bicyclo[1.1.1]pentan-1-yl)cyclopropane-1,1-dicarboxamide | 11 | +++ |
| N-(3-aminobicyclo[1.1.1]pentan-1-yl)-N-(4-((6,7-dimethoxyquinolin-4-yl)oxy)phenyl)cyclopropane-1,1-dicarboxamide | 12 | + |
| N-(3-acetamidobicyclo[1.1.1]pentan-1-yl)-N-(4-((6,7-dimethoxyquinolin-4-yl)oxy)phenyl)cyclopropane-1,1-dicarboxamide | 13 | + |
| N,N'-(bicyclo[1.1.1]pentane-1,3-diyl)bis(N-(4-((6,7-dimethoxyquinolin-4-yl)oxy)phenyl)cyclopropane-1,1-dicarboxamide) | 14 | + |
| methyl 4-(1-((4-((6,7-dimethoxyquinolin-4-yl)oxy)phenyl)carbamoyl)cyclopropane-1-carboxamido)bicyclo[2.2.2]octane-1-carboxylate | 15 | + |
| ethyl (2R,3R)-3-(1-((4-((6,7-dimethoxyquinolin-4-yl)oxy)phenyl)carbamoyl)cyclopropane-1-carboxamido)bicyclo[2.2.2]octane-2-carboxylate | 16 | + |
| N-(3-azabicyclo[3.1.0]hexan-1-yl)-N-(4-((6,7-dimethoxyquinolin-4-yl)oxy)phenyl)cyclopropane-1,1-dicarboxamide | 17 | + |
| N-(3-acetyl-3-azabicyclo[3.1.0]hexan-1-yl)-N-(4-((6,7-dimethoxyquinolin-4-yl)oxy)phenyl)cyclopropane-1,1-dicarboxamide | 18 | + |
| N-(4-((6,7-dimethoxyquinolin-4-yl)oxy)phenyl)-1-((1R,3r,5S)-3-methoxy-8-azabicyclo[3.2.1]octane-8-carbonyl)cyclopropane-1-carboxamide | 19 | + |
| 1-((1R,5S)-3-oxa-7-azabicyclo[3.3.1]nonane-7-carbonyl)-N-(4-((6,7-dimethoxyquinolin-4-yl)oxy)phenyl)cyclopropane-1-carboxamide | 20 | + |
| 1-(3-cyano-8-azabicyclo[3.2.1]octane-8-carbonyl)-N-(4-((6,7-dimethoxyquinolin-4-yl)oxy)phenyl)cyclopropane-1-carboxamide | 21 | + |
| (1R,5S,6r)-3-(1-((4-((6,7-dimethoxyquinolin-4-yl)oxy)phenyl)carbamoyl)cyclopropane-1-carbonyl)-3-azabicyclo[3.1.0]hexane-6-carboxamide | 22 | + |
| N-(4-((6,7-dimethoxyquinolin-4-yl)oxy)phenyl)-N-((1R,3r,5S)-8-methyl-8-azabicyclo[3.2.1]octan-3-yl)cyclopropane-1,1-dicarboxamide | 23 | + |
| N-(bicyclo[2.2.2]octan-1-yl)-N-(4-((6,7-dimethoxyquinolin-4-yl)oxy)phenyl)cyclopropane-1,1-dicarboxamide | 24 | ++ |
| N-((1s,4s)-bicyclo[2.2.1]heptan-1-yl)-N-(4-((6,7-dimethoxyquinolin-4-yl)oxy)phenyl)cyclopropane-1,1-dicarboxamide | 25 | +++ |
| 1-((1s,5s)-9-azabicyclo[3.3.1]nonane-9-carbonyl)-N-(4-((6,7-dimethoxyquinolin-4-yl)oxy)phenyl)cyclopropane-1-carboxamide | 26 | + |

TABLE 1-continued

Growth inhibition (GI$_{50}$) values for Representative Compounds against HCCLM3 cell lines.

| IUPAC name | Compound number | HCCLM3 activity range |
|---|---|---|
| 1-(3-azabicyclo[3.1.0]hexane-3-carbonyl)-N-(4-((6,7-dimethoxyquinolin-4-yl)oxy)phenyl)cyclopropane-1-carboxamide | 27 | + |
| N-((3R,5R)-adamantan-1-yl)-N-(4-((6,7-dimethoxyquinolin-4-yl)oxy)phenyl)cyclopropane-1,1-dicarboxamide | 28 | ++ |
| 3-(1-((4-((6,7-dimethoxyquinolin-4-yl)oxy)phenyl)carbamoyl)cyclopropane-1-carboxamido)bicyclo[1.1.1]pentane-1-carboxylic acid | 29 | + |
| N-(4-((6,7-dimethoxyquinolin-4-yl)oxy)phenyl)-N-(3-(methoxymethyl)bicyclo[1.1.1]pentan-1-yl)cyclopropane-1,1-dicarboxamide | 30 | ++ |
| methyl 3-(1-((4-((6,7-dimethoxyquinolin-4-yl)oxy)phenyl)carbamoyl)cyclopropane-1-carboxamido)bicyclo[1.1.1]pentane-1-carboxylate | 31 | +++ |
| N-(4-((6,7-dimethoxyquinolin-4-yl)oxy)phenyl)-N-(3-(hydroxymethyl)bicyclo[1.1.1]pentan-1-yl)cyclopropane-1,1-dicarboxamide | 32 | +++ |
| N-(3-cyanobicyclo[1.1.1]pentan-1-yl)-N-(4-((6,7-dimethoxyquinolin-4-yl)oxy)phenyl)cyclopropane-1,1-dicarboxamide | 33 | ++ |
| N$^1$-((1s,4s)-bicyclo[2.2.1]heptan-1-yl)-N$^3$-(4-((6,7-dimethoxyquinolin-4-yl)oxy)phenyl)bicyclo[1.1.1]pentane-1,3-dicarboxamide | 34 | + |
| 3-(3-azabicyclo[3.1.0]hexane-3-carbonyl)-N-(4-((6,7-dimethoxyquinolin-4-yl)oxy)phenyl)bicyclo[1.1.1]pentane-1-carboxamide | 35 | + |
| N$^1$-cyclopropyl-N$^3$-(4-((6,7-dimethoxyquinolin-4-yl)oxy)phenyl)bicyclo[1.1.1]pentane-1,3-dicarboxamide | 36 | + |

Example 2: Targeted Kinases

Exemplary kinase activity profile of compounds of formula (I) is shown below. Estimated IC$_{50}$ values are as shown in Table 2. As set forth in Table 2 below, IC$_{50}$ values are defined as follows: IC$_{50}$≤10 nM (+++); IC$_{50}$>10 nM and ≤30 nM (++); IC$_{50}$>800 nM (−).

TABLE 2

| Exemplary kinase activity profile | | |
|---|---|---|
| | Kinase | IC$_{50}$ (nM) |
| Trk family | TrkA (NTRK1) | +++ |
| | TrkB (NTRK2) | +++ |
| | TrkC (NTRK3) | +++ |
| VEGFR family | FLT1 (VEGFR1) | ++ |
| | VEGFR-2 (KDR) | ++ |
| | VEGFR-3 (FLT4) | +++ |
| Tyro (T), Axl (A) and Mer (M) family | Tyro3 | +++ |
| | Axl | +++ |
| | Mer | +++ |
| | c-KIT | − |

The invention claimed is:

1. A compound of formula (I) or a salt, solvate or prodrug thereof:

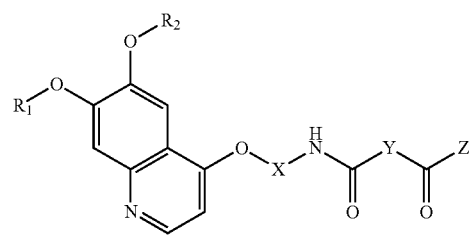

wherein R$_1$ and R$_2$ are independently selected from optionally substituted alkyl, optionally substituted alkenyl, and optionally substituted alkynyl;

X is selected from optionally substituted cycloalkylene, optionally substituted heterocyclylene, optionally substituted arylene, and optionally substituted heteroarylene;

Y is optionally substituted cycloalkylene; and

Z is selected from optionally substituted —N-heterocyclyl, optionally substituted —NH(heterocyclyl), optionally substituted —NH(cycloalkyl), optionally substituted —NH(aryl), and optionally substituted —NH(heteroaryl);

wherein at least one of X, Y and Z is an optionally substituted bridged moiety.

2. The compound, salt, solvate or prodrug according to claim 1, wherein:

X is selected from optionally substituted cycloalkylene and optionally substituted arylene; and Z is selected from optionally substituted —N-heterocyclyl, optionally substituted —NH(heterocyclyl), and optionally substituted —NH(cycloalkyl).

3. The compound, salt, solvate or prodrug according to claim 1, wherein $R_1$ and $R_2$ are independently optionally substituted $C_1$-$C_5$ alkyl.

4. The compound, salt, solvate or prodrug according to claim 1, wherein X is an optionally substituted bridged cycloalkylene or optionally substituted arylene.

5. The compound, salt, solvate or prodrug according to claim 1, wherein X is an optionally substituted bridged bicycloalkylene or optionally substituted arylene.

6. The compound, salt, solvate or prodrug according to claim 1, wherein X is an optionally substituted cycloalkylene or optionally substituted arylene, wherein the cycloalkylene or arylene is selected from the following:

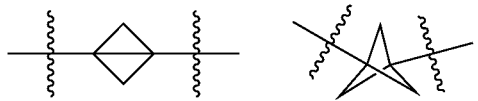

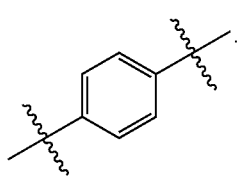

7. The compound, salt, solvate or prodrug according to claim 1, wherein Y is an optionally substituted cycloalkylene, wherein the cycloalkylene is selected from the following:

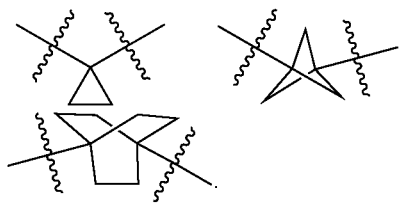

8. The compound, salt, solvate or prodrug according to claim 1, wherein Z is an optionally substituted bridged —N-heterocyclyl, or optionally substituted —NH(bridged cycloalkyl).

9. The compound, salt, solvate or prodrug according to claim 1, wherein Z is an optionally substituted bridged bicyclic —N-heterocyclyl, or optionally substituted —NH(bridged bicycloalkyl).

10. The compound, salt, solvate or prodrug according to claim 1, wherein Z is selected from the following:

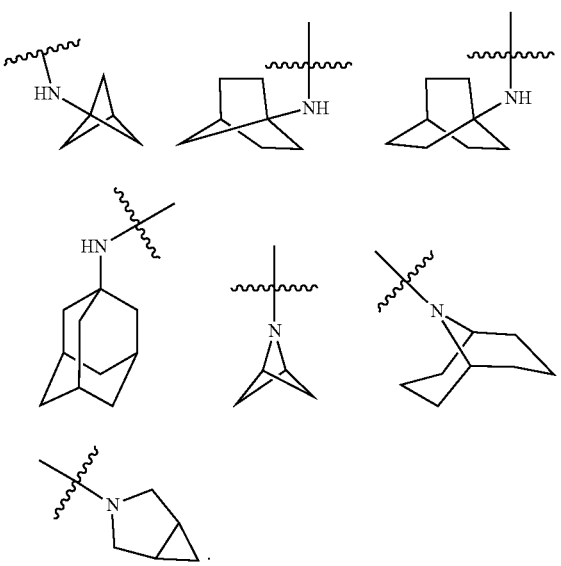

11. The compound, salt, solvate or prodrug according to claim 1, wherein Z is an optionally substituted —NH(bridged cycloalkyl).

12. The compound, salt, solvate or prodrug according to claim 1, wherein the compound is selected from the following:

1

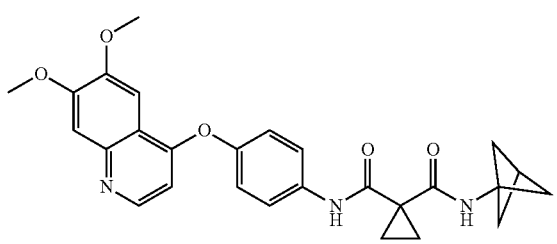

2

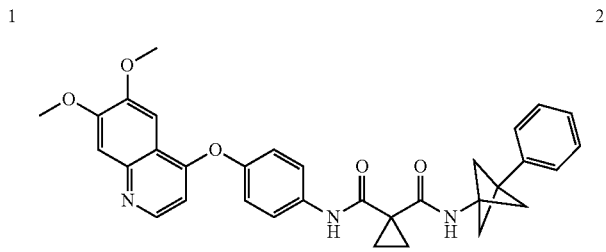

-continued
3
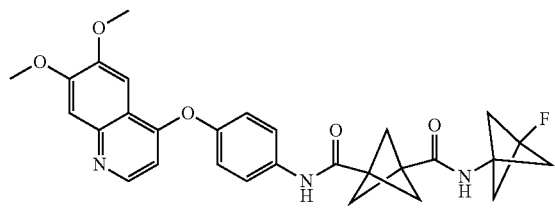
4
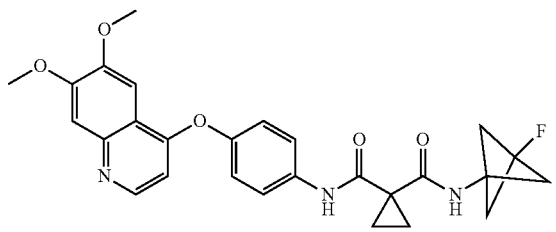
5
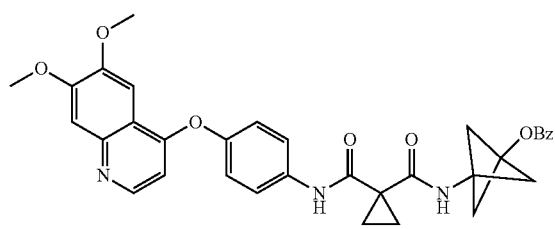
6
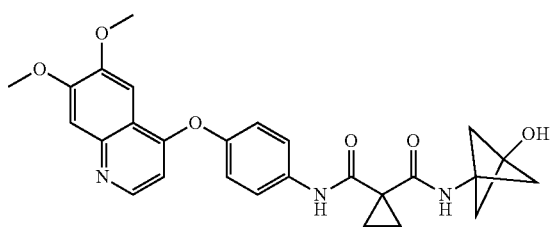
7
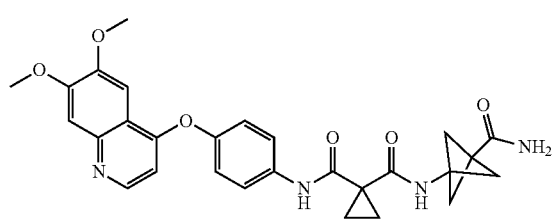
8
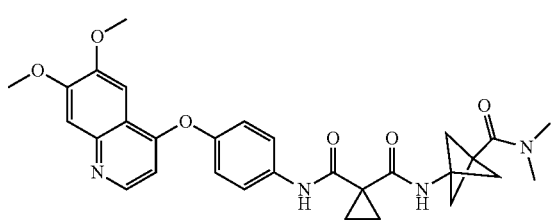
9
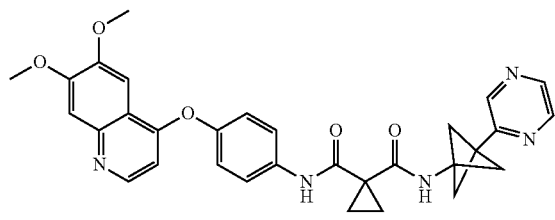
10
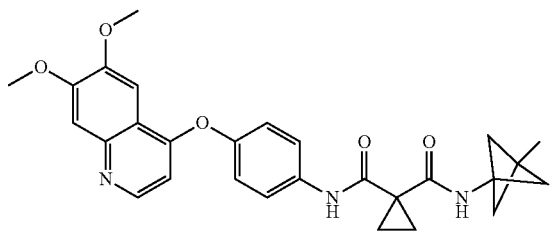
11
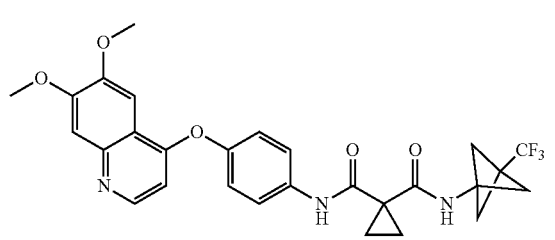
12
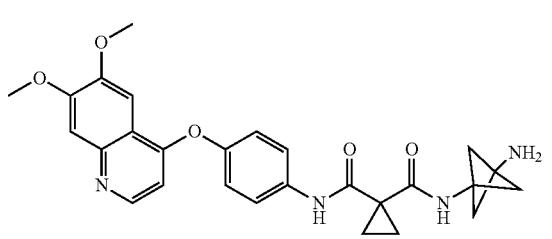
13
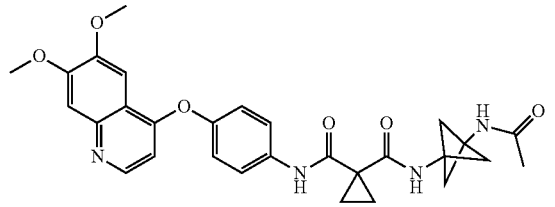

14
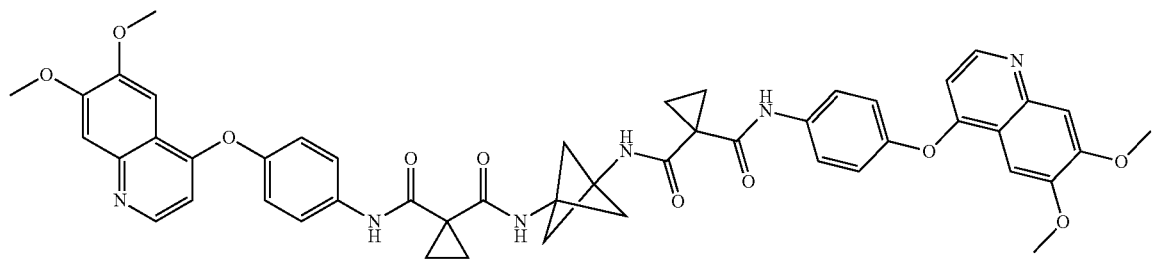
15
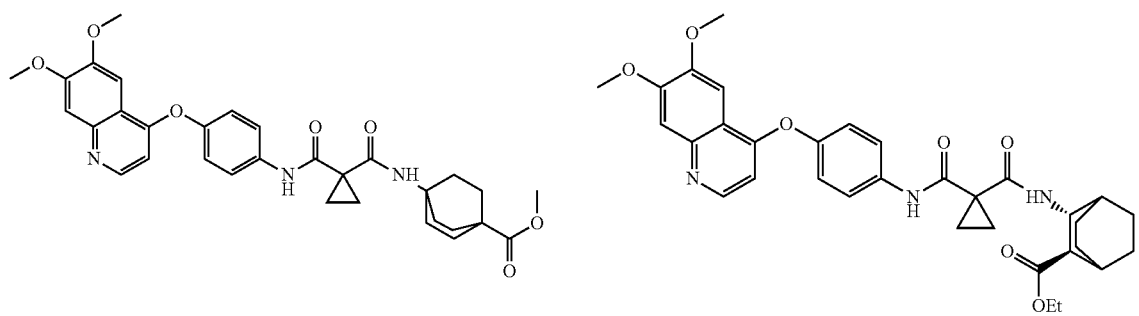
16
17
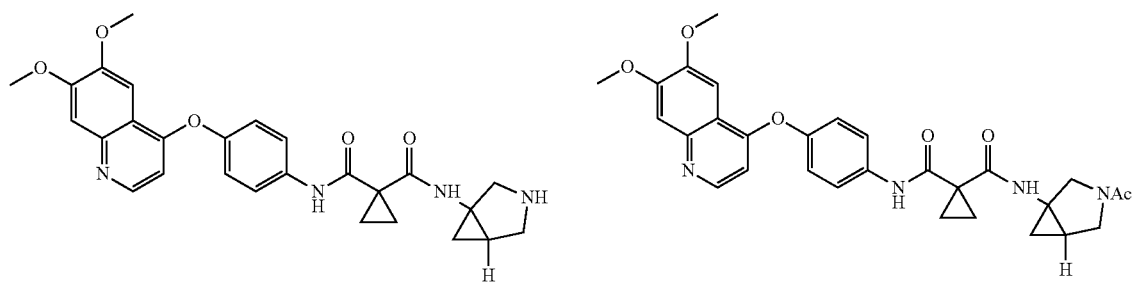
18
19
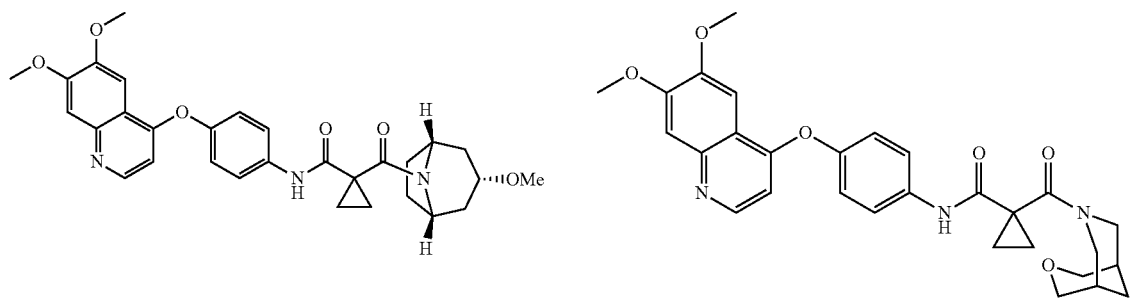
20
21
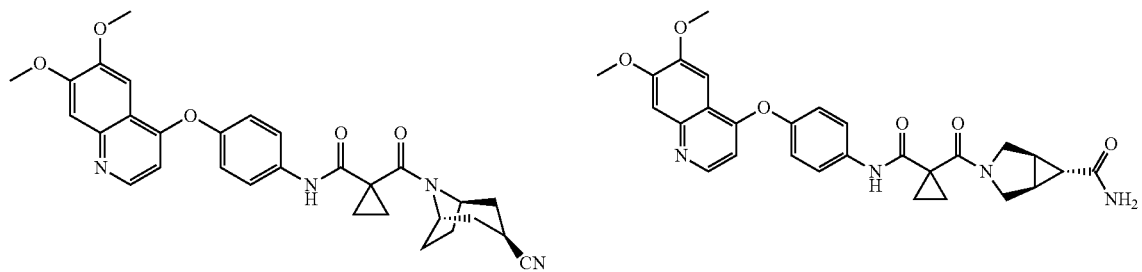
22

-continued
23
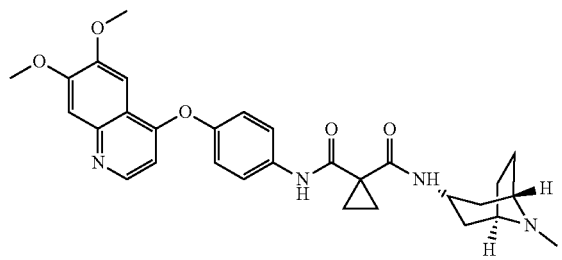
24
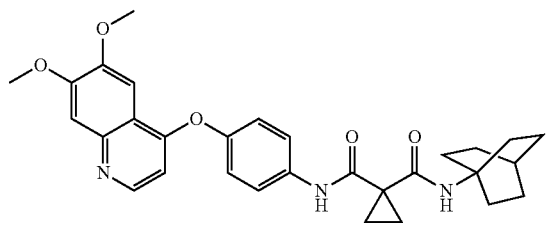
25
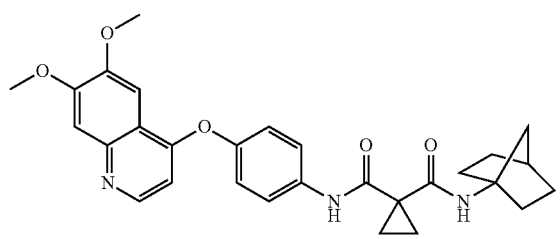
26
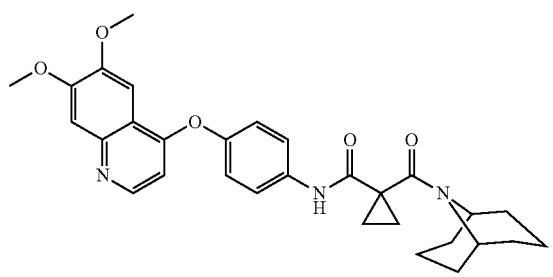
27
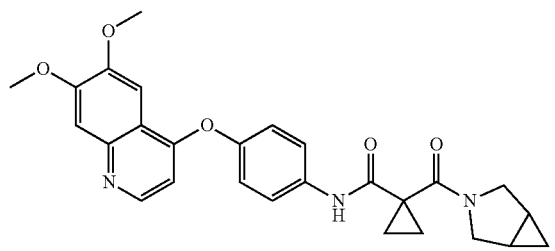
28
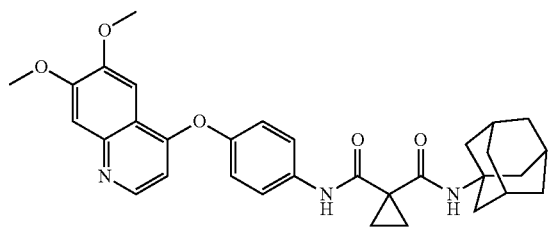
29
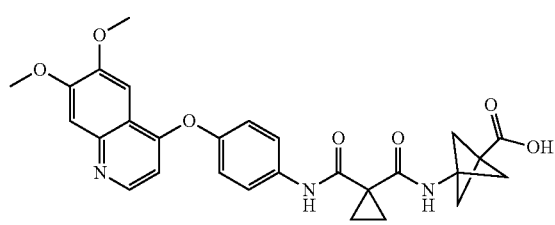
30
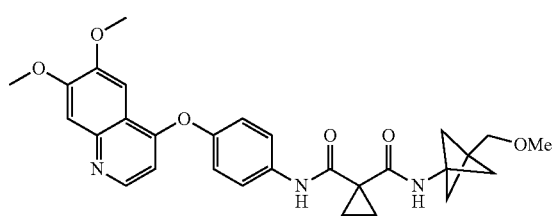
31
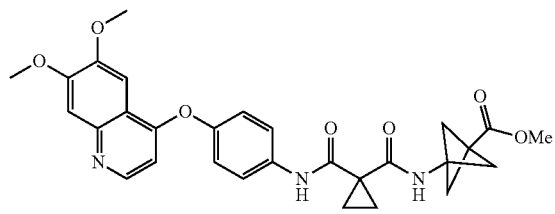
32
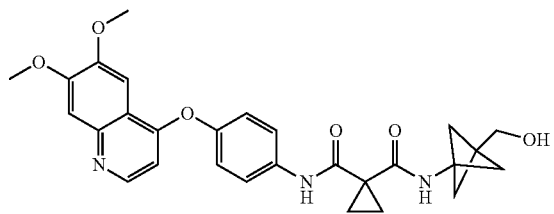
33
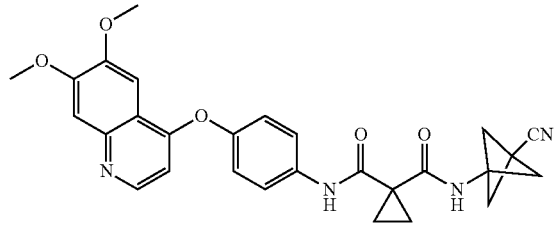
34
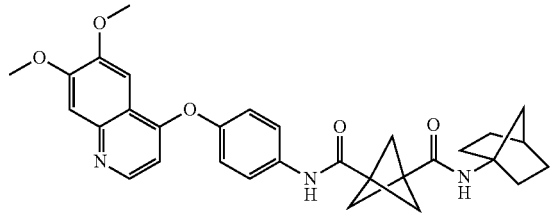

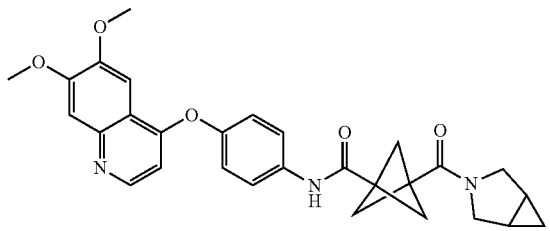
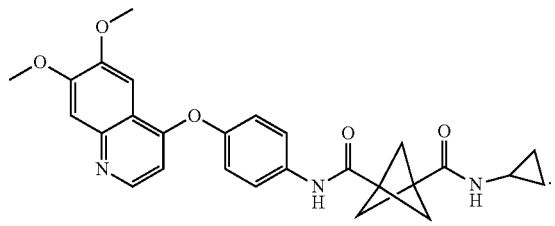

13. A pharmaceutical composition comprising an effective amount of a compound of formula (I) or a pharmaceutically acceptable salt, solvate or prodrug thereof:

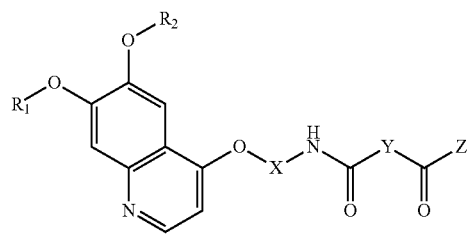

wherein R₁ and R₂ are independently selected from optionally substituted alkyl, optionally substituted alkenyl, and optionally substituted alkynyl;
X is selected from optionally substituted cycloalkylene, optionally substituted heterocyclylene, optionally substituted arylene, and optionally substituted heteroarylene;
Y is optionally substituted cycloalkylene; and
Z is selected from optionally substituted —N-heterocyclyl, optionally substituted NH(heterocyclyl), optionally substituted —NH(cycloalkyl), optionally substituted —NH(aryl), and optionally substituted —NH(heteroaryl);
wherein at least one of X, Y and Z is an optionally substituted bridged moiety.

14. A method for treating cancer in a patient in need thereof, the method comprising administering to the patient a therapeutically effective amount of a compound of formula (I) or a pharmaceutically acceptable salt, solvate or prodrug thereof:

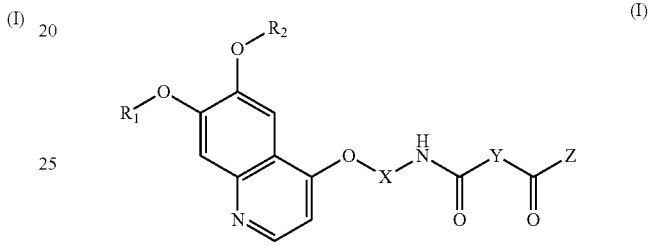

wherein R₁ and R₂ are independently selected from optionally substituted alkyl, optionally substituted alkenyl, and optionally substituted alkynyl;
X is selected from optionally substituted cycloalkylene, optionally substituted heterocyclylene, optionally substituted arylene, and optionally substituted heteroarylene;
Y is optionally substituted cycloalkylene; and
Z is selected from optionally substituted —N-heterocyclyl, optionally substituted —NH(heterocyclyl), optionally substituted —NH(cycloalkyl), optionally substituted —NH(aryl), and optionally substituted —NH(heteroaryl);
wherein at least one of X, Y and Z is an optionally substituted bridged moiety.

15. The method according to claim 14, wherein the cancer is hepatocellular carcinoma.

* * * * *